(12) United States Patent
Flynn et al.

(10) Patent No.: US 8,569,319 B2
(45) Date of Patent: Oct. 29, 2013

(54) PYRIDONE AMIDES AND ANALOGS EXHIBITING ANTI-CANCER AND ANTI-PROLIFERATIVE ACTIVITIES

(75) Inventors: Daniel L. Flynn, Lawrence, KS (US); Michael D. Kaufman, Lawrence, KS (US)

(73) Assignee: Deciphera Pharmaceuticals, LLS, Lawrence, KS (US)

(*) Notice: Subject to any disclaimer, the term of this patent is extended or adjusted under 35 U.S.C. 154(b) by 191 days.

(21) Appl. No.: 13/098,247

(22) Filed: Apr. 29, 2011

(65) Prior Publication Data
US 2012/0172382 A1 Jul. 5, 2012

Related U.S. Application Data

(60) Provisional application No. 61/329,542, filed on Apr. 29, 2010.

(51) Int. Cl.
*C07D 401/14* (2006.01)
*A61K 31/506* (2006.01)
*A61K 31/444* (2006.01)

(52) U.S. Cl.
USPC ............ 514/269; 514/333; 544/319; 546/256

(58) Field of Classification Search
USPC .................... 544/319; 546/256; 514/269, 333
See application file for complete search history.

(56) References Cited

U.S. PATENT DOCUMENTS

| | | | |
|---|---|---|---|
| 7,459,562 B2 | 12/2008 | Borzilleri et al. | |
| 7,851,489 B2 | 12/2010 | Borzilleri et al. | |
| 2003/0114435 A1 | 6/2003 | Tani et al. | |
| 2005/0245530 A1 | 11/2005 | Borzilleri et al. | |
| 2005/0288290 A1 | 12/2005 | Borzilleri et al. | |
| 2006/0004006 A1 | 1/2006 | Borzilleri et al. | |
| 2006/0211695 A1 | 9/2006 | Borzilleri et al. | |
| 2007/0060613 A1 | 3/2007 | Kim | |
| 2007/0123534 A1 | 5/2007 | Cai et al. | |
| 2007/0197537 A1 | 8/2007 | Blake et al. | |
| 2008/0004273 A1 | 1/2008 | Raeppel et al. | |
| 2008/0114033 A1 | 5/2008 | Borzilleri et al. | |
| 2008/0255155 A1 | 10/2008 | Raeppel et al. | |
| 2009/0012091 A1 | 1/2009 | Yu | |
| 2009/0105273 A1 | 4/2009 | Bolin et al. | |

FOREIGN PATENT DOCUMENTS

| | | |
|---|---|---|
| WO | WO 01/62708 A1 | 8/2001 |
| WO | WO 01/92235 A1 | 12/2001 |
| WO | WO 2005/030140 A2 | 4/2005 |
| WO | WO 2006/116713 A1 | 11/2006 |
| WO | WO 2007/033196 A1 | 3/2007 |
| WO | WO 2007/067444 A1 | 6/2007 |
| WO | WO 2007/076473 A2 | 7/2007 |
| WO | WO 2007/103308 A2 | 9/2007 |
| WO | WO 2007/146824 A2 | 12/2007 |
| WO | WO 2008/048375 A1 | 4/2008 |
| WO | WO 2008/057280 A1 | 5/2008 |
| WO | WO 2008/058229 A1 | 5/2008 |
| WO | WO 2008/063202 A2 | 5/2008 |
| WO | WO 2009/018657 A1 | 2/2009 |
| WO | WO 2009/033084 A1 | 3/2009 |
| WO | WO 2009/094417 A1 | 7/2009 |
| WO | WO 2009/094427 A1 | 7/2009 |
| WO | WO 2009/140549 A1 | 11/2009 |
| WO | WO 2010/051373 A1 | 5/2010 |

OTHER PUBLICATIONS

Ulrich, Chapter 4:Crystallization, Kirk-Othmer Encyclopedia of Chemical Technology, Aug. 2002.*
Vippagunta et al., Crystalline Solids, Advanced Drug Deliversy Reviews, 48, pp. 3-26, 2001.*
West, Solid Solutions, Solid State Chemistry and its applications, pp. 358 & 365, 1988.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1101 O, 1996.*
Pearce et al., Failure modes in anticancer drug discovery and development, Cancer Drug Design and Discovery Edited by Stephen Neidle, Chapter 18, pp. 424-435 (2008).*
Luo et al., Principles of Cancer Therapy: Oncogene and Non-oncogene Addiction, Cell, 136, pp. 823-837, Mar. 2009.*
Traxler, Protein Tyrosine Kinase inhibitors in cancer treatment, Expert Opinion on Therapeutic Patents, 7(6): 571-588, 1997.*
Damasio, Alzheimer's Disease and Related Dementias, Cecil Textbook of Medicine, 20th Edition, vol. 2, pp. 1992-1996 (1996).*
Layzer, Degenerative Diseases of the Nervous System, Cecil Textbook of Medicine, 20th Edition, vol. 2, pp. 2050-2057 (1996).*
Kim et al., "Discovery of Pyrrolopyridine—Pyridone Based Inhibitors of Met Kinase: Synthesis, X-ray Crystallographic Analysis, and Biological Activities," J. Med. Chem. 51:5330-5341 (2008).

(Continued)

Primary Examiner — Deepak Rao
(74) Attorney, Agent, or Firm — Cooley LLP

(57) ABSTRACT

Compounds useful in the treatment of mammalian cancers and especially human cancers according to Formula I are disclosed.

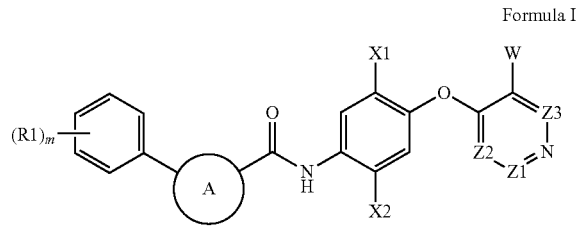

Formula I

Pharmaceutical compositions and methods of treatment employing the compounds disclosed herein are also disclosed.

23 Claims, No Drawings

(56) References Cited

OTHER PUBLICATIONS

Schroeder et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," J. Med. Chem. 52:1251-1254 (2009).

Lécaillon, "International Search Report," 4 pages, International Patent Application No. PCT/US2011/034550, European Patent Office (mailed Oct. 18, 2011).

Lécaillon, "Written Opinion of the International Searching Authority," 6 pages, International Patent Application No. PCT/US2011/034550, European Patent Office (mailed Oct. 18, 2011).

* cited by examiner

PYRIDONE AMIDES AND ANALOGS EXHIBITING ANTI-CANCER AND ANTI-PROLIFERATIVE ACTIVITIES

CROSS-REFERENCE TO RELATED APPLICATIONS

This application claims the benefit of U.S. Provisional Patent Application No. 61/329,542, filed Apr. 29, 2010, entitled "PYRIDONE AMIDES AND ANALOGS EXHIBITING ANTI-CANCER AND ANTI-PROLIFERATIVE ACTIVITIES," which is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_039_01US_SeqList_ST25.txt, date recorded: Jul. 13, 2011, file size 13 kilobytes).

FIELD

The present invention relates to kinase inhibitors exhibiting novel and unexpected properties useful for the treatment of various diseases including hyperproliferative diseases and cancer. More particularly, the invention is concerned with such compounds, methods of treating diseases, and methods of synthesis of the compounds. Preferably, the compounds are useful for the modulation of activity of c-MET kinase, c-MET kinase polymorphs, c-MET kinase mutants, or c-MET kinase fusion proteins in the treatment of mammalian diseases, and in particular human hyperproliferative diseases and human cancers. In some embodiments, compounds disclosed herein exhibit unexpected selectivity for modulation of c-MET kinase activity.

BACKGROUND c-MET is a receptor tyrosine kinase (RTK) located on chromosome 7p and activated via its natural ligand hepatocyte growth factor. c-MET is found mutated in a variety of solid tumors (Ma, P. C. et al. *Cancer Metastasis* (2003) 22: 309). Mutations in the tyrosine kinase domain are associated with hereditary papillary renal cell carcinomas (Schmidt, L. et al. *Nat. Genet.* (1997)16: 68; Schmidt, L. et al. *Oncogene* (1999) 18: 2343), whereas mutations in the sema and juxtamembrane domains are often found in small cell lung cancers (Ma, P. C. et al. *Cancer Res.* (2003) 63: 6272). Many activating mutations are also found in breast cancers (Nakopoulou, et al. *Histopath.* (2000) 36(4): 313). The panoply of tumor types for which c-MET mediated growth has been implicated suggests this is a target ideally suited for modulation by specific c-MET small molecule inhibitors.

The TPR-MET oncogene is a transforming variant of the c-MET RTK and was initially identified after treatment of a human osteogenic sarcoma cell line transformed by the chemical carcinogen N-methyl-N'-nitro-N-nitrosoguanidine (Park, M. et al. *Cell* (1986) 45: 895). The TPR-MET fusion oncoprotein is the result of a chromosomal translocation, placing the TPR3 locus on chromosome 1 upstream of a portion of the c-MET gene on chromosome 7 encoding only for the cytoplasmic region. Studies suggest that TPR-MET is detectable in experimental cancers (e.g., Yu, J. et al. *Cancer* (2000) 88: 1801). Dimerization of the $M_r$ 65,000 TPR-MET oncoprotein through a leucine zipper motif encoded by TPR leads to constitutive activation of the c-MET kinase (Zhen, Z. et al. *Oncogene* (1994) 9: 1691). TPR-MET activates wild-type c-MET RTK and can activate crucial cellular growth pathways, including the Ras pathway (Aklilu, F. et al. *Am. J. Physiol.* (1996) 271: E277) and the phosphatidylinositol 3-kinase (PI3K)/AKT pathway (Ponzetto, C. et al. *Mol. Cell. Biol.* (1993) 13: 4600). Conversely, in contrast to c-MET RTK, TPR-MET is ligand independent, lacks the CBL-like SH2 domain binding site in the juxtamembrane region in c-MET, and is mainly cytoplasmic. c-MET immunohistochemical expression seems to be associated with abnormal β-catenin expression, a hallmark feature of epithelial to mesenchymal transition (EMT) and provides good prognostic and predictive factors in breast cancer patients.

In human therapeutics, it is desirable to provide small molecule inhibitors of a protein target within in a protein family which do not cross-inhibit closely related protein family members. These closely related protein family members are often referred to as 'off-targets', to distinguish them from the essential target of interest referred to as the 'on target' of the inhibitor. A small molecule which inhibits multiple protein family members, while being potent against the target of interest, can be limited in its utility as a human therapeutic due to unintended side effects and toxicities introduced due to the consequences of inhibition of these 'off targets.'

Protein kinases constitute an important therapeutic protein family. There are approximately 518 human protein kinases. While inhibition of a desired kinase 'on target' is desirable for a human therapeutic, it is also desirable in many cases to provide a selective kinase inhibitor which does not substantially inhibit other kinase 'off targets' from within this protein family. Monoclonal antibodies are one approach to providing specific inhibitors to a specific kinase without inhibiting 'off targets.' Achieving this level of selectivity with small molecule inhibitors, however, is not as easily achievable nor as straightforward. Accordingly, there is a need for kinase inhibitors that are selective for a particular protein kinase. It is theorized that an unexpected increase in potency for c-MET kinase inhibition or an unexpected increase in selective c-MET inhibition relative to other kinases is observed for one or more of the embodiments disclosed herein.

SUMMARY

Compounds described herein find utility in the treatment of mammalian cancers and especially human cancers including, but not limited to, solid tumors, gastric cancers, melanomas, glioblastomas, ovarian cancer, pancreatic cancer, prostate cancer, lung cancers, non small cell lung cancer, breast cancers, kidney cancers, cervical carcinomas, metastasis of primary tumor sites, colonic cancers, myeloproliferative diseases, diseases wherein the etiology or progression is dependent on c-MET kinase activity, or on the activity of oncogenic forms-, aberrant fusion protein forms-, and mutant forms of c-MET kinase.

Specifically, pyridone amide compounds of Formula I are disclosed which find utility in the treatment of diseases as described above.

Formula I

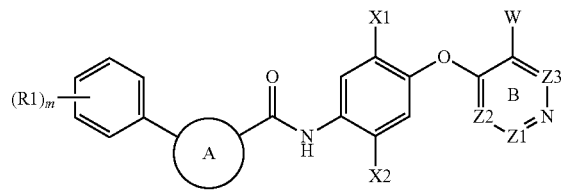

-continued

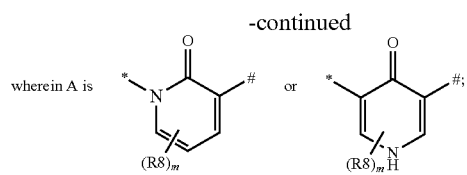

wherein the "*" is connected to the R1-substituted phenyl ring and the "#" is connected to the amide carbonyl; and R1, R8, m, X1, X2, W, Z1, Z2, and Z3 are as defined below for Formula I.

More specifically, pyridone amide compounds of Formula II and Formula III are disclosed:

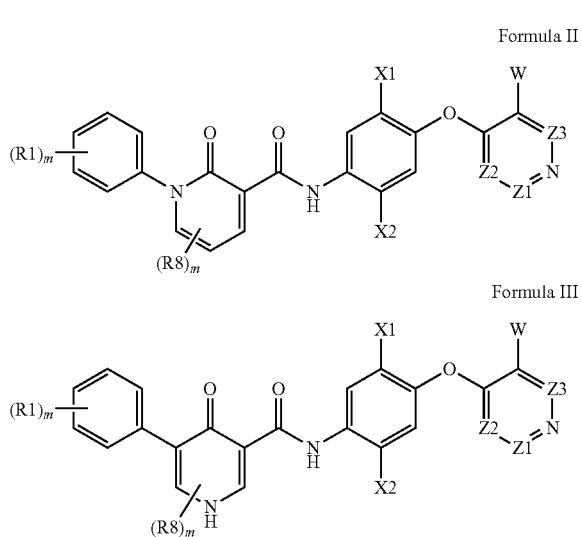

Accordingly, in one aspect, the present invention comprises a compound of Formula I.

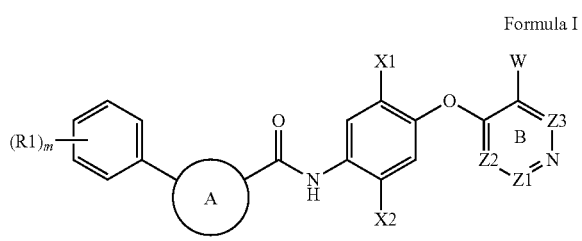

or a pharmaceutically acceptable salt, hydrate, solvate, enantiomer, stereoisomer or tautomer thereof, wherein:
A is

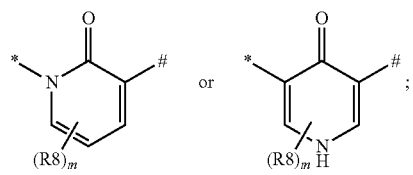

wherein the "*" is connected to the R1-substituted phenyl ring and the "#" is connected to the amide carbonyl;
W is $-(CH_2)_m$-pyrazole optionally substituted with $-(R25)_m$;

X1 is halogen or C1-C6 alkyl;
X2 is halogen or C1-C6 alkyl;
each R1 is individually and independently halogen, H, C1-C6 alkyl, C3-C8 branched alkyl, C3-C8 cycloalkyl, C1-C6 alkoxy, branched C3-C6 alkoxy, or cyano;
Z1 and Z2 are independently and individually CR2 or N;
Z3 is CR3 or N;
with the proviso that ring B is a monocyclic ring which is not a tetrazine;
each R2 is individually and independently H, halogen, C1-C6 alkyl, C3-C8 branched alkyl, C3-C8 cycloalkyl, C1-C6 alkoxy, branched C3-C6 alkoxy, or cyano;
R3 is —NHR4, H, —NR6(R7), C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, (R7)R6N—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, wherein
aryl is phenyl, naphthyl, tetrahydronaphthyl, indenyl or indanyl; and
each alkyl or alkylene is optionally substituted with one or two C1-C6 alkyl;
R4 is H, C1-C8 alkyl, C3-C8 cycloalkyl, —(CH$_2$)$_m$—C(O) R5, —(CH$_2$)$_p$—OR6, —(CH$_2$)$_p$—NR6(R7), —(CH$_2$)$_p$—CN, —(CH$_2$)$_p$—SO$_2$—C1-C6-alkyl, C6-C10 aryl, —(CH$_2$)$_m$—C5-C6-heteroaryl, —(CH$_2$)$_m$—C4-C6-heterocyclyl, —(CH$_2$)$_m$—C(O)N(R6)-C4-C6-heterocyclyl, or —(CH$_2$)$_m$—C(O)N(R6)-C5-C6-heteroaryl, wherein each alkyl or alkylene is optionally substituted with one or two C1-C6 alkyl;
R5 is C1-C7 alkyl, branched C3-C8 alkyl, C3-C8 cycloalkyl, —(CH$_2$)$_m$—OR6, —(CH$_2$)$_m$—NR6(R7), C6-C10 aryl, —(CH$_2$)$_m$—C5-C6-heteroaryl, or —(CH$_2$)$_m$—C4-C6-heterocyclyl, wherein
aryl is phenyl, naphthyl, tetrahydronaphthyl, indenyl or indanyl; and
each alkyl or alkylene is optionally substituted with one or two C1-C6 alkyl;
each R6 and R7 is individually and independently H, C1-C6 alkyl, or branched C3-C8 alkyl;
each R8 is individually and independently C1-C6 alkoxy, H, halogen, C1-C6 alkyl, C3-C8 branched alkyl, C3-C8 cycloalkyl, branched C3-C6 alkoxy, or cyano;
each alkynyl, cycloalkyl, aryl, heteroaryl and heterocyclyl is independently and optionally substituted with —(R25)$_m$;
each R25 is individually and independently C1-C6 alkyl, branched C3-C8 alkyl, halogen, —(CH$_2$)$_m$—CN, —(CH$_2$)$_m$—OR6, —(CH$_2$)$_m$—NR6(R7), —(CH$_2$)$_m$—C(O)NR6(R7), —(CH$_2$)$_m$—C(O)$_m$—C4-C6-heterocyclyl, or —(CH$_2$)$_m$—C4-C6-heterocyclyl, wherein each alkyl or alkylene is optionally substituted with one or two C1-C6 alkyl;
each m is individually and independently 0, 1, 2, or 3;
n is 0, 1, or 2; and
each p is individually and independently 1, 2, or 3.
In some embodiments, the compound of Formula I is a compound of Formula Ia,

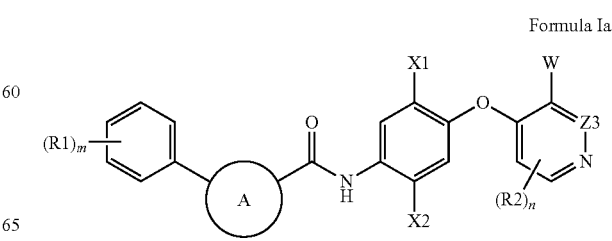

or a pharmaceutically acceptable salt, hydrate, solvate, enantiomer, stereoisomer or tautomer thereof.

In some embodiments of the compound of Formula Ia, Z3 is CR3.

In some embodiments, the compound of Formula Ia is a compound of Formula Ib,

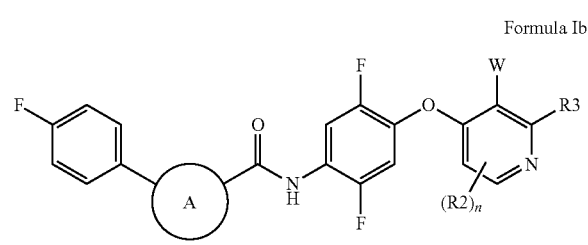

Formula Ib or a pharmaceutically acceptable salt, hydrate, solvate, enantiomer, stereoisomer or tautomer thereof.

In some embodiments of the compound of Formula Ib, R3 is —NHR4.

In some embodiments of the compound of Formula Ib, R3 is H.

In some embodiments of the compound of Formula Ib, R3 is —NR6(R7), (R7)R6N—C1-C6-alkyl-, C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, wherein each alkyl or alkylene is optionally substituted with one or two C1-C6 alkyl.

In some embodiments of the compound of Formula Ib, W is

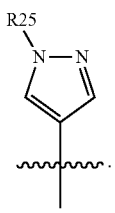

In some embodiments of the compound of Formula Ia, Z3 is CR3 and W is

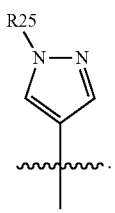

In some embodiments of the compound of Formula Ib, the A ring is

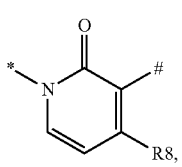

and R8 is C1-C6 alkoxy.

In some embodiments of the compound of Formula Ib, the A ring is

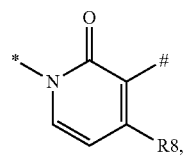

and R8 is ethoxy.

In some embodiments of the compound of Formula Ia, Z3 is N.

In some embodiments of the compound of Formula Ia, the compound is a compound of Formula Ic,

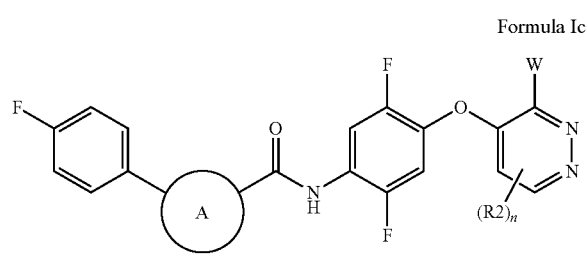

Formula Ic or a pharmaceutically acceptable salt, hydrate, solvate, enantiomer, stereoisomer or tautomer thereof.

In some embodiments of the compound of Formula Ic, W is

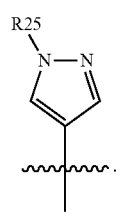

In some embodiments of the compound of Formula Ia, Z3 is N and W is

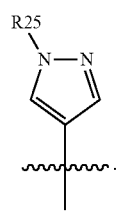

In some embodiments of the compound of Formula Ic, the A ring is

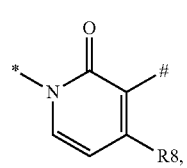

and R8 is C1-C6 alkoxy.

In some embodiments of the compound of Formula Ic, the A ring is

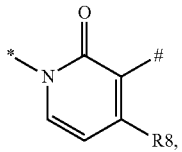

and R8 is ethoxy.

In some embodiments of the compound of Formula I, Z1 is CR2, Z2 is N, and Z3 is CR3.

In some embodiments of the compound of Formula I, the compound is a compound of Formula Id,

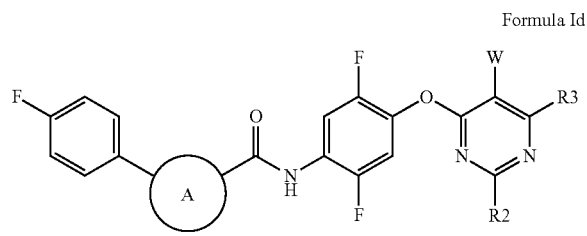

Formula Id or a pharmaceutically acceptable salt, hydrate, solvate, enantiomer, stereoisomer or tautomer thereof.

In some embodiments of the compound of Formula Id, R3 is —NHR4.

In some embodiments of the compound of Formula Id, R3 is H.

In some embodiments of the compound of Formula Id, R3 is —NR6(R7), C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, (R7)R6N—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, and wherein each alkyl or alkylene is optionally substituted with one or two C1-C6 alkyl.

In some embodiments of the compound of Formula Id, W is

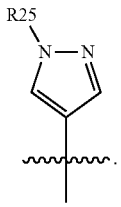

In some embodiments of the compound of Formula I, Z1 is CR2, Z2 is N, and Z3 is CR3 and W is

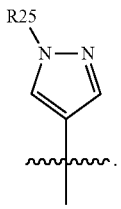

In some embodiments of the compound of Formula Id, the A ring is

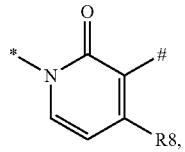

and R8 is C1-C6 alkoxy.

In some embodiments of the compound of Formula Id, the A ring is

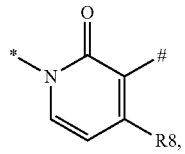

and R8 is ethoxy.

In some embodiments, the invention comprises a compound selected from the group consisting of N-(2,5-difluoro-4-(5-(1-methyl-1H-pyrazol-4-yl)pyrimidin-4-yloxy)phenyl)-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-1-(4-fluorophenyl)-2-oxo-1,2-dihydropyridine-3-carboxamide, N-(4-(3-(1-(cyanomethyl)-1H-pyrazol-4-yl)pyridin-4-yloxy)-2,5-difluorophenyl)-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(4-(2-amino-3-(1-methyl-1H-pyrazol-4-yl)pyridin-4-yloxy)-2,5-difluorophenyl)-1-(4-fluorophenyl)-2-oxo-1,2-dihydropyridine-3-carboxamide, N-(5-chloro-2-fluoro-4-(3-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-5-(4-fluorophenyl)-1-methyl-4-oxo-1,4-dihydropyridine-3-carboxamide, N-(4-(2-amino-3-(1-methyl-1H-pyrazol-4-yl)pyridin-4-yloxy)-2,5-difluorophenyl)-4-ethoxy-1-(4-fluorophenyl)-2-oxo-1,2-dihydropyridine-3-carboxamide, N-(4-(3-(1H-pyrazol-4-yl)pyridin-4-yloxy)-2,5-difluorophenyl)-4-ethoxy-1-(4-fluorophenyl)-2-oxo-1,2-dihydropyridine-3-carboxamide, N-(4-(2-amino-3-(1-methyl-1H-pyrazol-4-yl)pyridin-4-yloxy)-2,5-difluorophenyl)-5-(4-fluorophenyl)-1-methyl-4-oxo-1,4-dihydropyridine-3-carboxamide and pharmaceutically acceptable salts, solvates, hydrates and tautomers thereof.

In certain embodiments, the invention comprises a method of treating mammalian disease wherein the disease etiology or progression is at least partially mediated by a kinase activity, wherein the kinase is a wildtype form, a mutant oncogenic form, an aberrant fusion protein form or a polymorph, the method comprising administering to a mammal in need thereof an effective amount of a compound of any of claims 1-27.

In certain embodiments, the disease etiology or progression is at least partially mediated by the kinase activity of c-MET, mutant oncogenic forms, aberrant fusion proteins, or polymorphs thereof.

In other embodiments, the present invention comprises a pharmaceutical composition, comprising a compound of any of claims 1-27 and a pharmaceutically acceptable carrier.

In certain embodiments, the composition comprises an additive selected from adjuvants, excipients, diluents, or stabilizers.

In some embodiments, the invention includes a method of treating cancer, gastrointestinal stromal tumors, hyperproliferative diseases, metabolic diseases, neurodegenerative diseases, or diseases characterized by angiogenesis, such as solid tumors, melanomas, glioblastomas, ovarian cancer, pancreatic cancer, prostate cancer, lung cancers, breast cancers, renal cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, colonic cancers, ocular diseases characterized by hyperproliferation leading to blindness including retinopathies, diabetic retinopathy, age-related macular degeneration, hypereosinophilic syndrome, rheumatoid arthritis, asthma, chronic obstructive pulmonary, mastocytosis, or mast cell leukemia, the method comprising administering to a patient in need thereof an effective amount of a compound of any of claims 1-27.

In certain embodiments of the present methods, the compound is administered orally, parenterally, by inhalation, or subcutaneously.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, pharmaceutically acceptable salts, and solvates thereof, as well as crystalline polymorphic forms of the disclosed compounds and any and all possible isomers, stereoisomers, enantiomers, diastereomers, tautomers, pharmaceutically acceptable salts, and solvates thereof. Thus, the terms "compound" and "compounds" as used in this disclosure refer to the compounds of this disclosure and any and all possible isomers, stereoisomers, enantiomers, diastereomers, tautomers, pharmaceutically acceptable salts, solvates, and crystalline polymorphs thereof.

Definitions

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —$CH_2$—, —$CH_2CH_2$—, and —$CH_2CH_2CH_2$—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized $\pi$ electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands. For example, in some embodiments, a ring N atom from the heterocyclyl is the bonding atom to —C(O) to form an amide, carbamate, or urea. In exemplary embodiments, "heterocyclyl" refers to a cyclic hydrocarbon as described above containing 4, 5, or 6 ring atoms (i.e., C4-C6 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands. For example, in some embodiments, a ring N atom from the heteroaryl is the bonding atom to —C(O) to form an amide, carbamate, or urea. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline, earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term "subject" includes, without limitation, a human or an animal. Exemplary animals include, but are not limited to, mammals such as mouse, rat, guinea pig, dog, cat, horse, cow, pig, monkey, chimpanzee, baboon, or rhesus monkey.

The term "treating" as used herein with regard to a subject, refers to improving at least one symptom of the subject's disorder. Treating can be curing, improving, or at least partially ameliorating the disorder.

The term "hydrate" as used herein refers to a compound disclosed herein which is associated with water in the molecular form, i.e., in which the H—OH bond is not split, and may be represented, for example, by the formula R.H$_2$O, where R is a compound disclosed herein. A given compound may form more than one hydrate including, for example, monohydrates (R.H$_2$O), dihydrates (R.2H$_2$O), trihydrates (R.3H$_2$O), and the like.

The term "solvate" as used herein refers to a compound disclosed herein which is associated with solvent in the molecular form, i.e., in which the solvent is coordinatively hound, and may be represented, for example, by the formula R.(solvent), where R is a compound disclosed herein. A given compound may form more than one solvate including, for example, monosolvates (R.(solvent)) or polysolvates (R.n (solvent)) wherein n is an integer greater than 1) including, for example, disolvates (R.2(solvent)), trisolvates (R.3(solvent)), and the like, or hemisolvates, such as, for example, R.n/2(solvent), R.n/3(solvent), R.n/4(solvent) and the like, wherein n is an integer. Solvents herein include mixed solvents, for example, methanol/water, and as such, the solvates may incorporate one or more solvents within the solvate.

The term "acid hydrate" as used herein refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is $H^+$, is also known as "prototropy." Tautomers are defined as isomers that arise from tautomerism, independent of whether the isomers are isolable.

ChemDraw version 8.0 or 10, (CambridgeSoft Corporation, Cambridge, Mass.) was used to name structures.

The following abbreviations are used in this disclosure and have the following definitions: ADP is adenosine diphosphate, ATP is adenosine triphosphate, DIEA is N,N-diisopropylethylamine, DMA is N,N-dimethylacetamide, DMF is N,N-dimethylformamide, DMSO is dimethylsulfoxide, DTT is dithiothreitol, ESI is electrospray ionization, EtOAc is ethyl acetate, GST is glutathione S-transferase, "h" is hour or hours, $IC_{50}$ is half maximal inhibitory concentration, min is minutes, MS is mass spectrometry, NADH is nicotinamide adenine dinucleotide, NMR is nuclear magnetic resonance, PBS is phosphate buffered saline, RT is room temperature, TBTU is O-(Benzotriazol-1-yl)-N,N,N',N'-tetramethyluronium tetrafluoroborate, THF is tetrahydrofuran, and Tris is tris(hydroxymethyl)aminomethane.

Compounds

In one aspect, compounds of the Formula I are described:

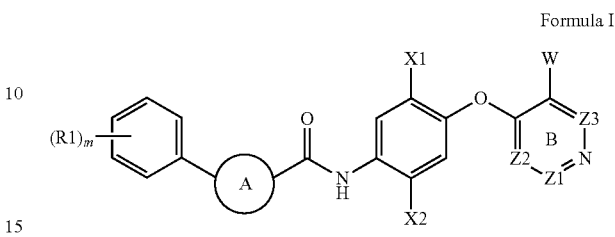

Formula I and pharmaceutically acceptable salts, hydrates, solvates, enantiomers, stereoisomers, and tautomers thereof:

wherein

A, W, X1, X2, Z1, Z2, Z3, R1, R2, R3, R4, R5, R6, R7, R8, R25, m, n, and p are as defined above for Formula I; and each heterocyclyl and heteroaryl individually and independently has a C or N bonding hand.

In some embodiments, a ring N atom from the heterocyclyl is the bonding atom to —C(O) to form an amide, carbamate, or urea. In other embodiments, a ring N atom from the heteroaryl is the bonding atom to —C(O) to form an amide, carbamate, or urea.

In some embodiments, compounds of the Formula I are compounds of the Formula II:

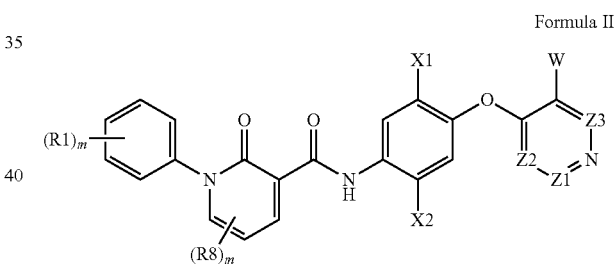

Formula II wherein

W, X1, X2, Z1, Z2, Z3, R1, R2, R3, R4, R5, R6, R7, R8, R25, m, n, and p are as defined above for Formula I.

In further embodiments, compounds of the Formula I are compounds of the Formula III:

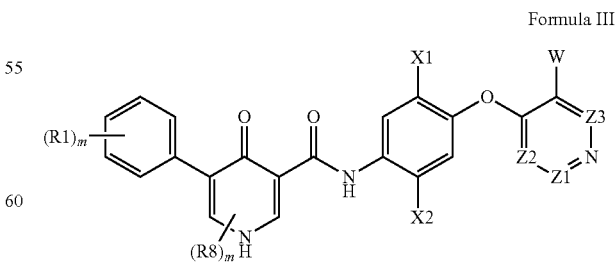

Formula III wherein

W, X1, X2, Z1, Z2, Z3, R1, R2, R3, R4, R5, R6, R7, R8, R25, m, n, and p are as defined above for Formula I.

In some embodiments, compounds of the Formula II are compounds of the Formula IIa:

Formula IIa wherein
W, X1, X2, Z3, R1, R2, R3, R4, R5, R6, R7, R8, R25, m, n, and p are as defined above for Formula I.

In some embodiments, compounds of the Formula II are compounds of the Formula IIb:

Formula IIb wherein
W, R2, R3, R4, R5, R6, R7, R8, R25, m, n, and p are as defined above for Formula I.

In some embodiments, compounds of the Formula II are compounds of the Formula IIc:

Formula IIc wherein
X1, X2, R1, R2, R3, R4, R5, R6, R7, R8, R25, m, n, and p are as defined above for Formula I; and
W is —(CH$_2$)$_m$-pyrazole optionally substituted with —(R25)$_m$.

In some embodiments, compounds of the Formula II are compounds of the Formula IIc.1:

Formula IIc.1 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is H.

In some embodiments, compounds of the Formula II are compounds of the Formula IIc.2:

Formula IIc.2 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, —NR6(R7), (R7)R6N—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, wherein each alkyl or alkylene is optionally substituted with one or two C1-C6 alkyl.

In some embodiments, compounds of the Formula II are compounds of the Formula IIc.3:

Formula IIc.3 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is —NR6(R7) or —NHR4.

In some embodiments, compounds of the Formula II are compounds of the Formula IId:

Formula IId wherein
X1, X2, R1, R2, R3, R4, R5, R6, R7, R8, R25, m, n, and p are as defined above for Formula I.

In some embodiments, compounds of the Formula II are compounds of the Formula IId.1:

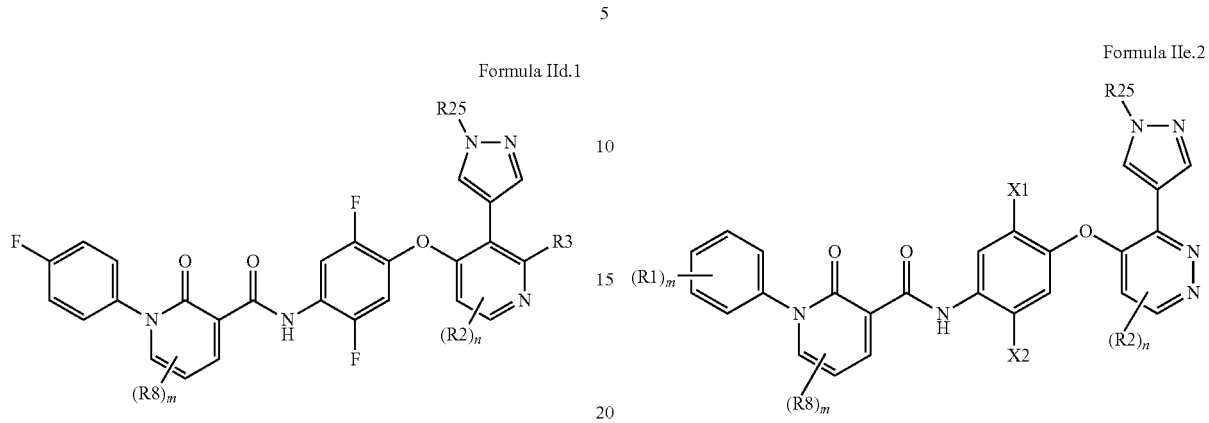

Formula IId.1 wherein
R2, R3, R4, R5, R6, R7, R8, R25, m, n, and p are as defined above for Formula I.

In some embodiments, compounds of the Formula II are compounds of the Formula IIe:

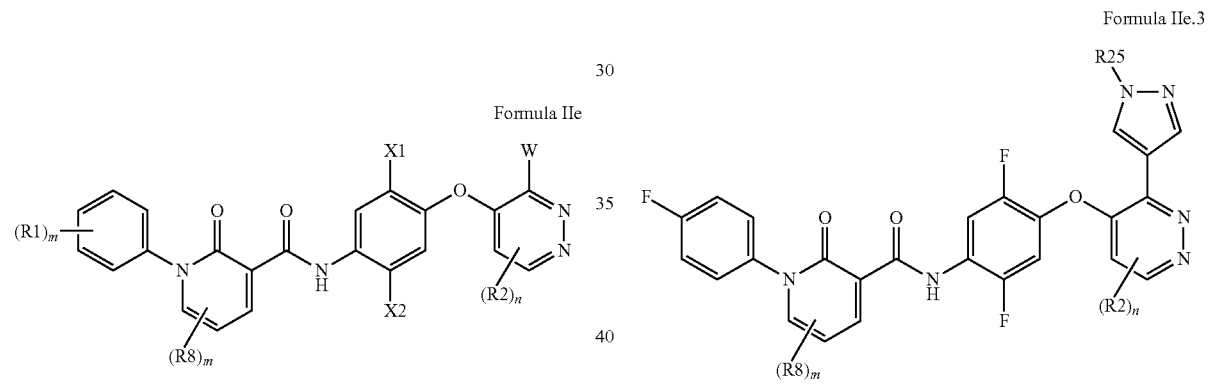

Formula IIe wherein
W, X1, X2, R1, R2, R8, R25, m, n, and p are as defined above for Formula I.

In some embodiments, compounds of the Formula II are compounds of the Formula IIe.1:

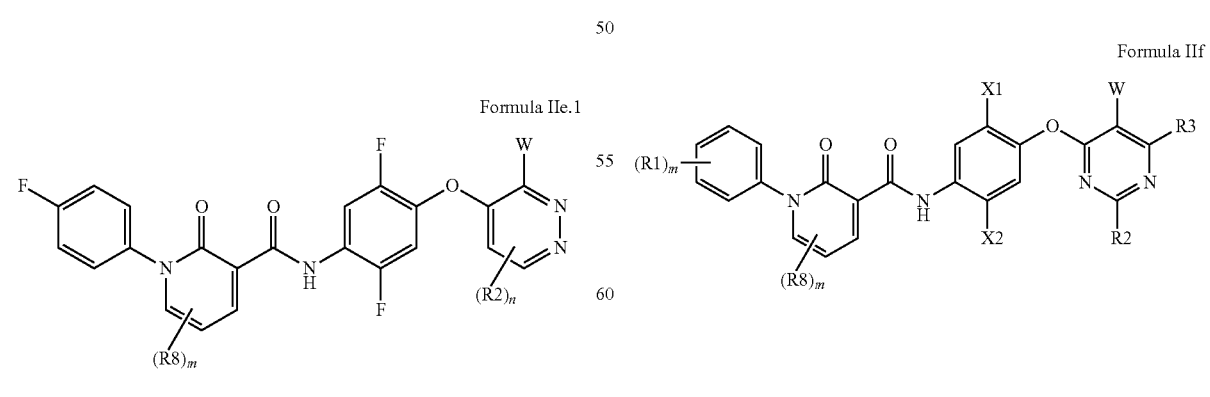

Formula IIe.1 wherein
W, R2, R8, R25, m, n, and p are as defined above for Formula I.

In some embodiments, compounds of the Formula II are compounds of the Formula IIe.2:

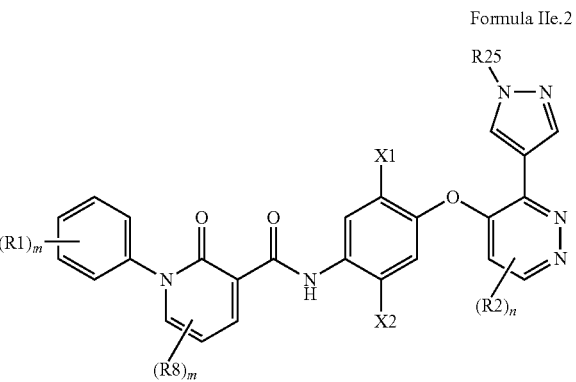

Formula IIe.2 wherein
X1, X2, R1, R2, R8, R25, m, n, and p are as defined above for Formula I.

In some embodiments, compounds of the Formula II are compounds of the Formula IIe.3:

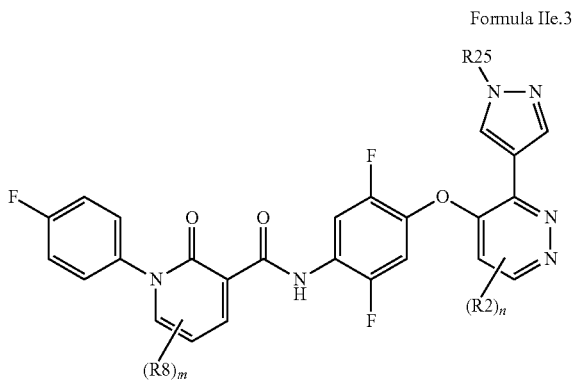

Formula IIe.3 wherein
R2, R8, R25, m, and n are as defined above for Formula I.

In some embodiments, compounds of the Formula II are compounds of the Formula IIf:

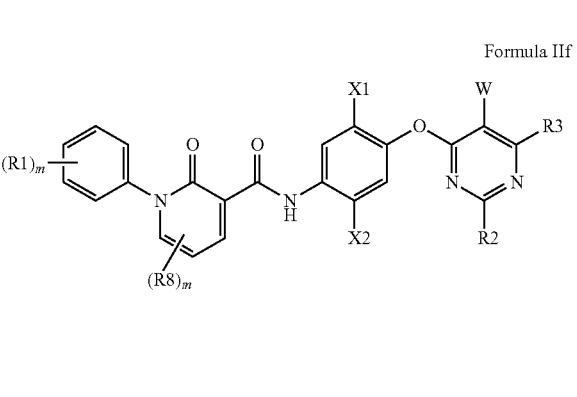

Formula IIf wherein
W, X1, X2, R1, R2, R3, R4, R5, R6, R7, R8, R25, m, n, and p are as defined above for Formula I.

In some embodiments, compounds of the Formula II are compounds of the Formula IIf.1:

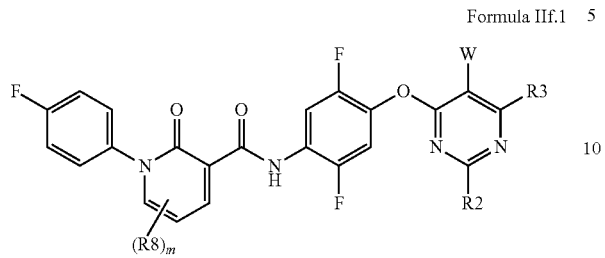

Formula IIf.1 wherein
W, R2, R3, R4, R5, R6, R7, R8, R25, m, n, and p are as defined above for Formula I.

In some embodiments, compounds of the Formula II are compounds of the Formula IIf.2:

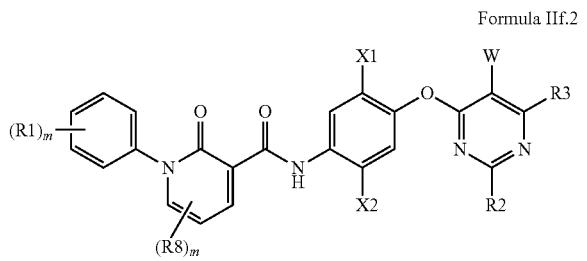

Formula IIf.2 wherein
X1, X2, R1, R2, R.4, R5, R6, R7, R8, R25, m, and p are as defined above for Formula I;
W is —(CH$_2$)$_m$-pyrazole optionally substituted with —(R25)$_m$; and
R3 is H.

In some embodiments, compounds of the Formula II are compounds of the Formula IIf.3:

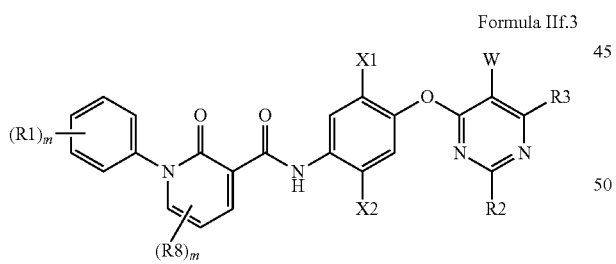

Formula IIf.3 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, —NR6 (R7), (R7)R6N—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, wherein each alkyl or alkylene is optionally substituted with one or two C1-C6 alkyl.

In some embodiments, compounds of the Formula II are compounds of the Formula IIf.4:

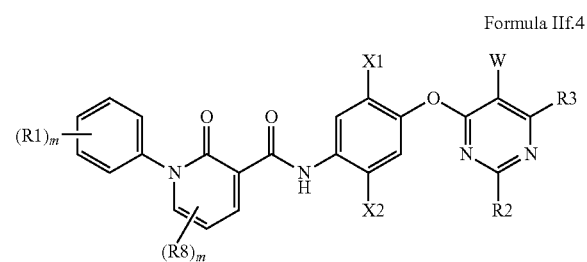

Formula IIf.4 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is —NR6(R7) or —NHR4.

In some embodiments, compounds of the Formula II are compounds of the Formula IIf.5:

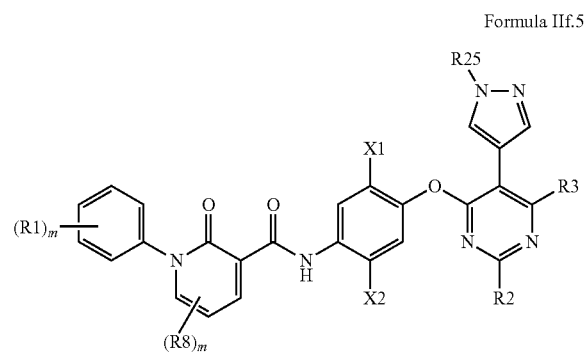

Formula IIf.5 wherein
X1, X2, R1, R2, R3, R4, R5, R6, R7, R8, R25, m, n, and p are as defined above for Formula I.

In some embodiments, compounds of the Formula II are compounds of the Formula IIf.6:

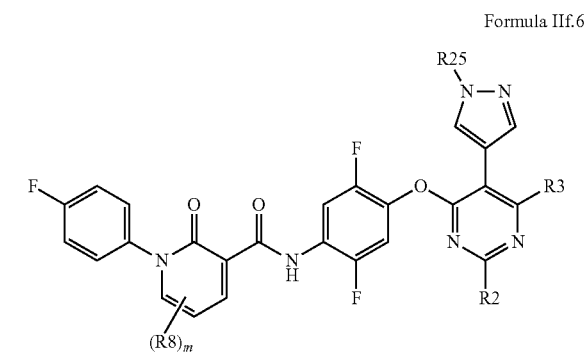

Formula IIf.6 wherein
R2, R3, R4, R5, R6, R7, R8, R25, m, n, and p as defined above for Formula I.

In some embodiments, compounds of the Formula III are compounds of the Formula IIIa:

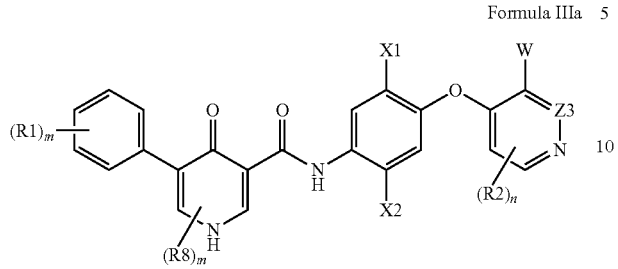

Formula IIIa wherein
W, X1, X2, Z3, R1, R2, R3, R4, R5, R6, R7, R8, R25, m, n, and p are as defined above for Formula I.

In some embodiments, compounds of the Formula III are compounds of the Formula IIIb:

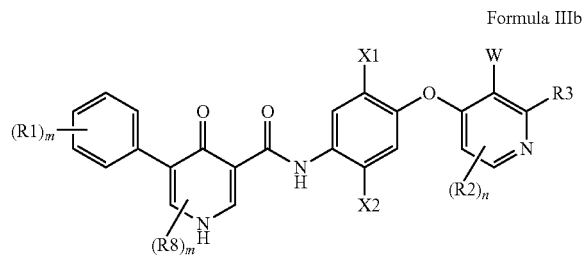

Formula IIIb wherein
W, X1, X2, R1, R2, R3, R4, R5, R6, R7, R8, R25, m, n, and p are as defined above for Formula I.

In some embodiments, compounds of the Formula III are compounds of the Formula IIIc:

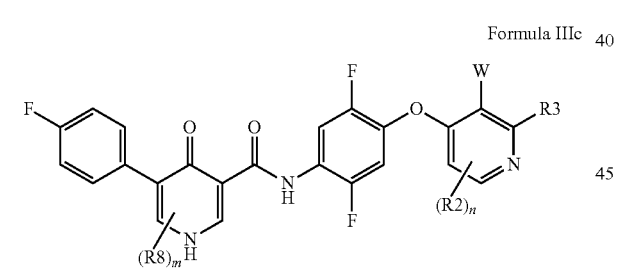

Formula IIIc wherein
W, R2, R3, R4, R5, R6, R7, R8, R25, m, n, and p are as defined above for Formula I.

In some embodiments, compounds of the Formula III are compounds of the Formula IIId:

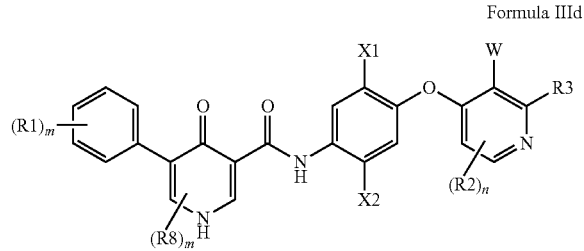

Formula IIId wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is H.

In some embodiments, compounds of the Formula III are compounds of the Formula IIId.1:

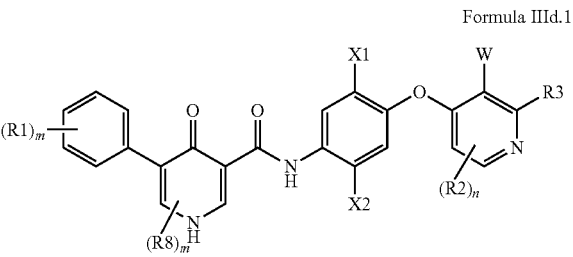

Formula IIId.1 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, —NR6(R7), (R7)R6N—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, wherein each alkyl or alkylene is optionally substituted with one or two C1-C6 alkyl.

In some embodiments, compounds of the Formula III are compounds or the Formula IIId.2:

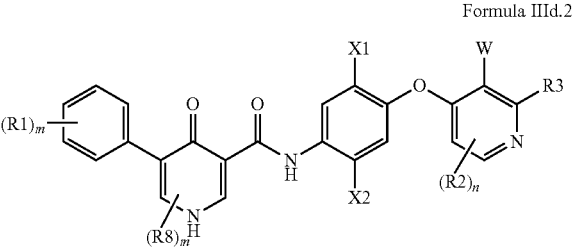

Formula IIId.2 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is —NR6(R7) or —NHR4.

In some embodiments, compounds of the Formula III are compounds of the Formula IIIe:

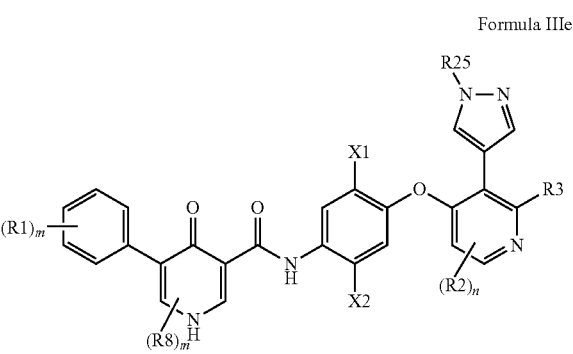

Formula IIIe wherein

X1, X2, R1, R2, R3, R4, R5, R6, R7, R8, R25, m, n, and p are as defined above for Formula I.

In some embodiments, compounds of the Formula III are compounds of the Formula IIIe.1:

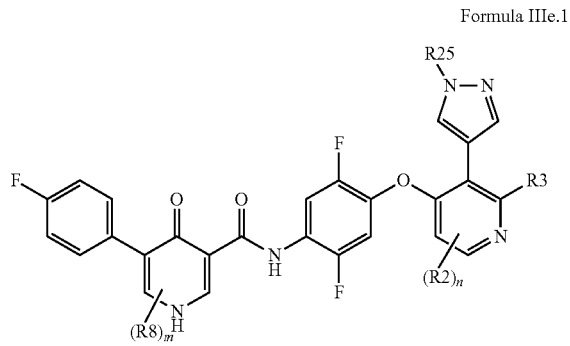

Formula IIIe.1 wherein

R2, R3, R4, R5, R6, R7, R8, R25, m, n, and p are as defined above for Formula I.

In some embodiments, compounds of the Formula III are compounds of the Formula IIIf:

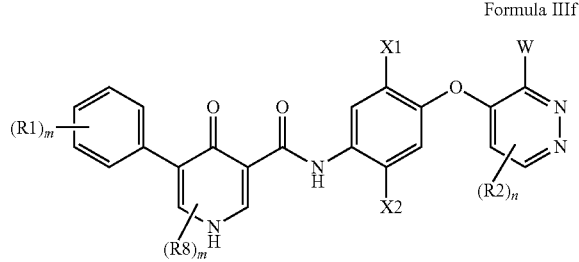

Formula IIIf wherein

W, X1, X2, R1, R2, R8, R25, m, n, and p are as defined above for Formula I.

In some embodiments, compounds of the Formula III are compounds of the Formula IIIf.1:

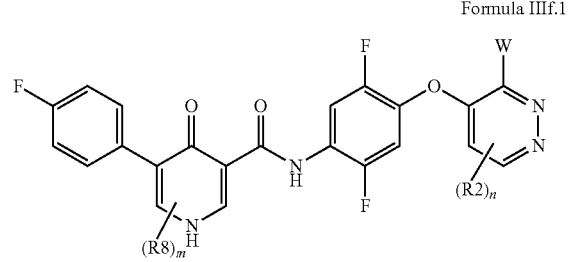

Formula IIIf.1 wherein

W, R2, R8, R25, m, n, and p are as defined above for Formula I.

In some embodiments, compounds of the Formula III are compounds of the Formula IIIf.2:

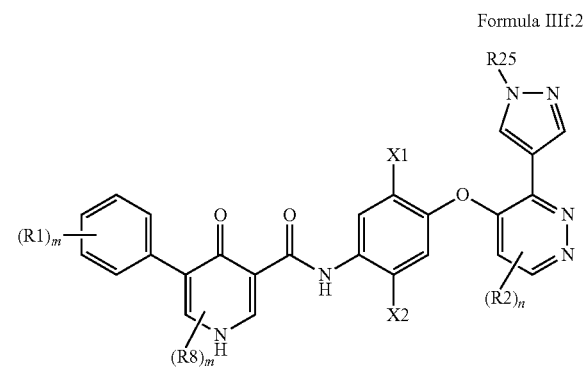

Formula IIIf.2 wherein

X1, X2, R1, R2, R8, R25, m, n, and p are as defined above for Formula I.

In some embodiments, compounds of the Formula III are compounds of the Formula IIIf.3:

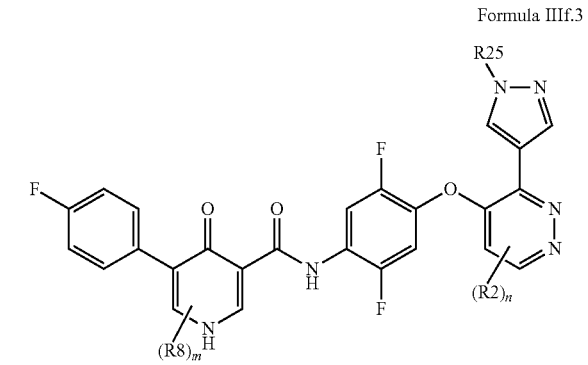

Formula IIIf.3 wherein

R2, R8, R25, m, n, and p are as defined above for Formula I.

In some embodiments, compounds of the Formula III are compounds of the Formula IIIg:

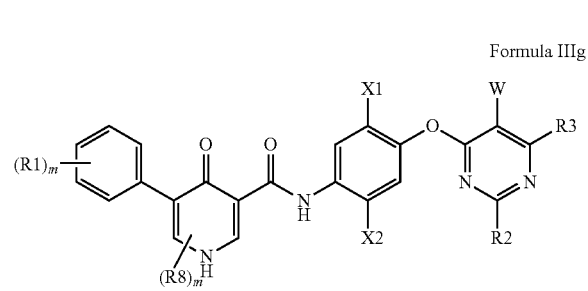

Formula IIIg wherein

W, X1, X2, R1, R2, R3, R4, R5, R6, R7, R8, R25, m, n, and p are as defined above for Formula I.

In some embodiments, compounds of the Formula III are compounds of the Formula IIIg.1:

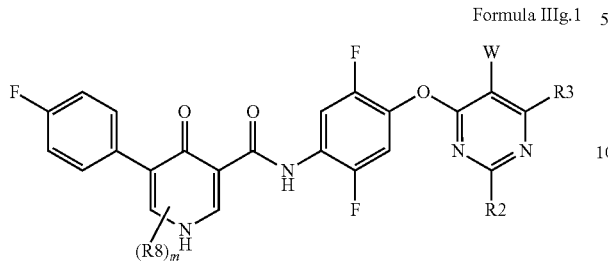

Formula IIIg.1 wherein
W, R2, R3, R4, R5, R6, R7, R8, R25, m, n, and p are as defined above for Formula I.

In some embodiments, compounds of the Formula III are compounds of the Formula IIIg.2:

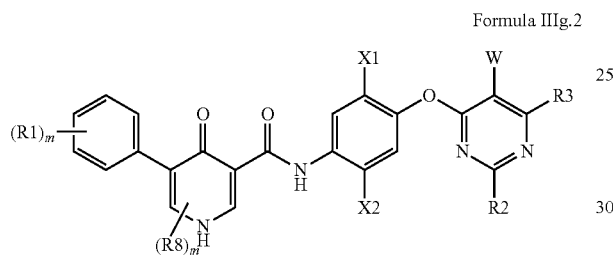

Formula IIIg.2 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is H.

In some embodiments, compounds of the Formula III are compounds of the Formula IIIg.3:

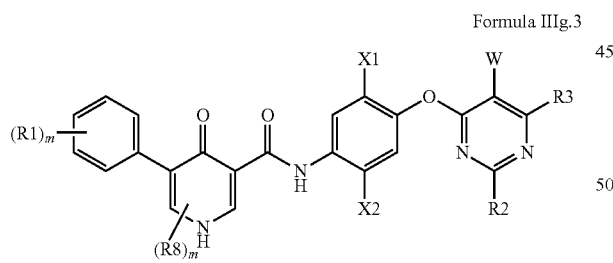

Formula IIIg.3 wherein
X1, X2, R1, R2, R4, R5, R6, R7, R8, R25, m, and p are as defined above for Formula I;
W is —(CH$_2$)$_m$-pyrazole optionally substituted with —(R25)$_m$; and
R3 is C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, —NR6(R7), (R7)R6N—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, wherein each alkyl or alkylene is optionally substituted with one or two C1-C6 alkyl.

In some embodiments, compounds of the Formula III are compounds of the Formula IIIg.4:

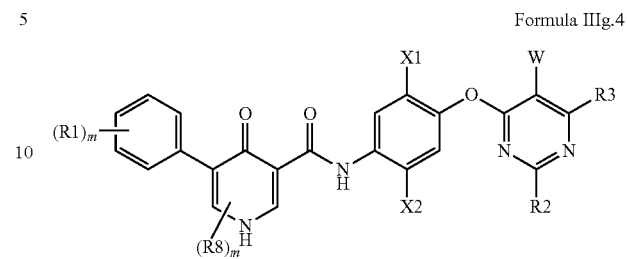

Formula IIIg.4 wherein
X1, X2, R1, R2, R4, R5, R6, R7, R8, R25, m, n, and p are as defined above for Formula I;
W is —(CH$_2$)$_m$-pyrazole optionally substituted with —(R25)$_m$; and
R3 is —NR6(R7) or —NHR4.

In some embodiments, compounds of the Formula III are compounds of the Formula IIIg.5:

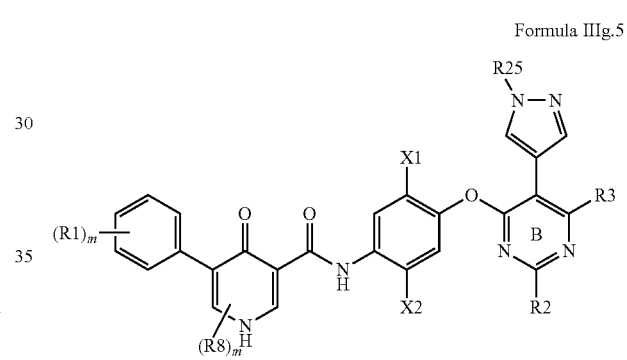

Formula IIIg.5 wherein
B, X1, X2, R1, R2, R3, R4, R5, R6, R7, R8, R25, m, n and p are as defined above for Formula I.

In some embodiments, compounds of the Formula III are compounds of the Formula IIIg.6:

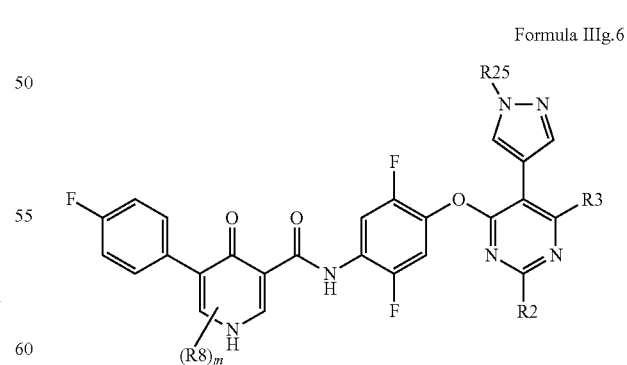

Formula IIIg.6 wherein
R2, R3, R4, R5, R6, R7, R8, R25, m, n and p are as defined above for Formula I.

The following embodiments are descriptive of Formula I, Formula II, Formula IIa, Formula IIc, Formula IIc.1, Formula IIc.2, Formula IIc.3, Formula IId, Formula IId.1, Formula IIe, Formula IIe.2, Formula IIf, Formula IIf.2, Formula IIf.3, Formula IIf.4, Formula IIf.5, Formula III, Formula IIIa, Formula IIIb, Formula IIId, Formula IIId.2, Formula IIIe, Formula IIIf, Formula IIIf.2, Formula IIIg, Formula IIIg.2, Formula IIIg.3, Formula IIIg.4 and Formula IIIg.5.

In some embodiments, each X1 and X2 is individually and independently halogen. In other embodiments, each X1 and X2 is individually and independently F or Cl. In further embodiments, each X1 and X2 is F.

In some embodiments, each R1 is individually and independently halogen. In other embodiments, each R1 is individually and independently F or Cl. In further embodiments, each R1 is F.

In some embodiments, m is 1 and R1 is halogen. In other embodiments, m is 1 and R1 is F or Cl. In further embodiments, m is 1 and R1 is F.

In some embodiments, each R1, X1 and X2 is individually and independently halogen. In other embodiments, each R1, X1 and X2 is individually and independently F or Cl. In further embodiments, each R1, X1 and X2 is F.

In some embodiments, m is 1 and each R1, X1 and X2 is individually and independently halogen. In other embodiments, m is 1 and each R1, X1 and X2 is individually and independently F or Cl. In further embodiments m is 1 and each R1, X1 and X2 is F.

Utility

Compounds described herein find utility in the treatment of mammalian cancers and especially human cancers including, but not limited to, solid tumors, gastric cancers, melanomas, glioblastomas, ovarian cancer, pancreatic cancer, prostate cancer, lung cancers, non small cell lung cancer, breast cancers, kidney cancers, cervical carcinomas, metastasis of primary tumor sites, colonic cancers, myeloproliferative diseases, diseases wherein the etiology or progression is dependent on c-MET kinase activity, or on the activity of oncogenic forms-, aberrant fusion protein forms, and mutant forms of c-MET kinase.

Administration of Compounds

In some embodiments, the compound is administered by a method selected from the group consisting of oral, parenteral, inhalation, and subcutaneous.

Treatment Methods

The disclosed methods also include treating individuals suffering from a condition selected from the group consisting of cancer, hyperproliferative diseases, metabolic diseases, neurodegenerative diseases or diseases characterized by angiogenesis. These methods comprise administering to such individuals compounds disclosed herein, and especially those of section I, said diseases including, but not limited to, solid tumors, malignant melanomas, glioblastomas, ovarian cancer, pancreatic cancer, prostate cancer, lung cancers, breast cancers, kidney cancers, hepatic cancers; cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, gastrointestinal stromal tumors, colonic cancers, ocular diseases characterized by hyperproliferation leading to blindness including various retinopathies, diabetic retinopathy and age-related macular degeneration and hypereosinophilic syndrome, rheumatoid arthritis, asthma, chronic obstructive pulmonary disorder, mastocytosis, mast cell leukemia, a disease caused by c-c-MET kinase, oncogenic forms thereof, aberrant fusion proteins thereof and polymorphs thereof. The administration method is not critical, and may be from the group consisting of oral, parenteral, inhalation, and subcutaneous.

Pharmaceutical Preparations

The compounds disclosed herein may form a part of a pharmaceutical composition by combining, one or more such compounds with a pharmaceutically acceptable carrier. Additionally, the compositions may include an additive selected from the group consisting of adjuvants, excipients, diluents, and stabilizers.

Methods of Making

The compounds of the invention are available by the general synthetic methods illustrated in the Schemes below and the accompanying examples.

Compounds 1 of the invention are assembled in a step-wise manner as illustrated in Scheme 1. Acids of formula 2 are reacted with amines of formula 3 in the presence of standard peptide coupling reagents familiar to those skilled in the art to prepare amides of formula 1. Suitable reagents for the conversion of 2 to 1 include TBTU (O-(benzotriazol-1-yl)-N,N,N',N'-tetramethyluronium tetrafluoroborate), PyBOP (benzotriazol-1-yloxy)tripyrrolidinophosphonium hexafluorophosphate), EDC (1-ethyl-3-(3-dimethylaminopropyl)carbodiimide hydrochloride) and BOP—Cl (bis(2-oxo-3-oxazolidinyl)phosphonic chloride). It is recognized that in this case and in others to follow, a carboxylic acid moiety, such as found in 2, can also be activated as an acid halide, anhydride, mixed anhydride, or as an activated ester (for example a pentafluorophenyl ester). Those skilled in the art will recognize that such activated esters can react directly with amine 3 in the absence of an added peptide coupling reagent. In the case of activated acid derivatives it will be further understood that these compounds are optionally isolated as discrete intermediates prior to their union with amines 3 to form 1. Using similar conditions, acids of formula 5 also are, in some embodiments, coupled with amine 3 to yield amides 4, additional compounds of the invention.

Scheme 1

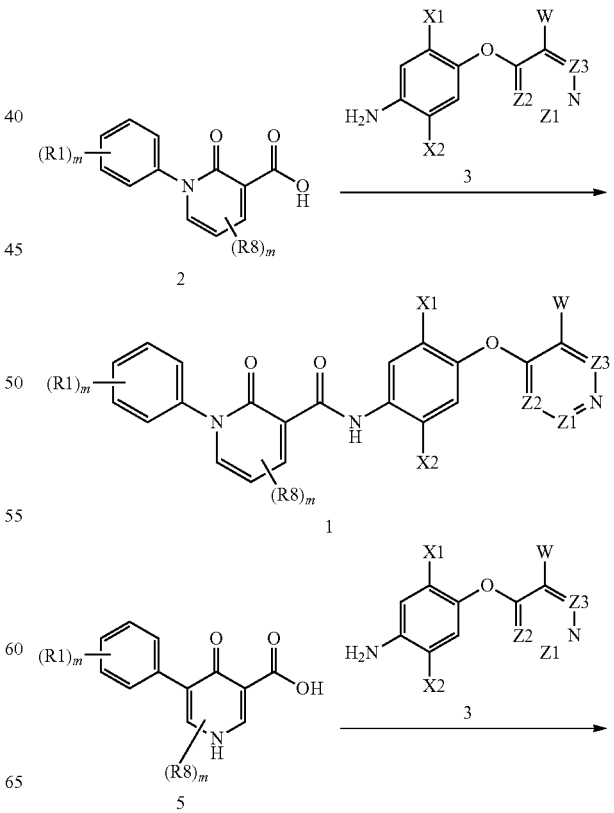

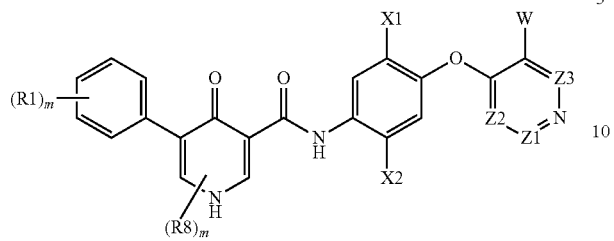

Non-limiting examples of Scheme 1 are illustrated in Scheme 2 for the preparation of compound 8, an example of general formula 1 (wherein R1 is 4-fluoro, m is 1, R8 is H, X1 and X2 are fluoro, Z1 and Z3 are CH, Z2 is N, and W is N-methyl-4-pyrazolyl) and compound 10, an example of general formula 4 (wherein R1 is 4-fluoro, m is 1, R8 is H, X1 and X2 are fluoro, Z1 and Z3 are CH, Z2 is N, and W is N-methyl-4-pyrazolyl). Thus, the combination of acid 6 (an example of general acid 2) and amine 7 (an example of general amine 3) in the presence of a peptide coupling agent, for example TBTU, provides amide 8. Using similar conditions, acid 9 (an example of general acid 5) is converted to amide 4.

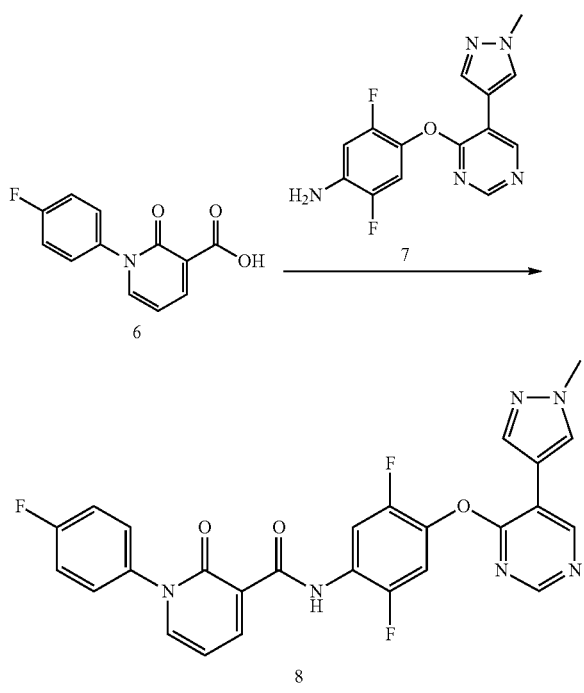

Amines 3 useful for the invention are synthesized according to methods commonly known to those skilled in the art. Amines 3 contain a central ether moiety and in general terms are prepared by the reaction of amino-phenol 11 or nitrophenol 12 with a pyridine, pyrimidine, pyridazine or triazine of general formula 13, wherein the LG-moiety of 13 represents a leaving group such as a halide or sulfonate that is displaced in a nucleophilic aromatic substitution reaction and the L-moiety of 13 is either the W-group of compound 1 or a functional group that is readily converted to the NV-group of formula 1 by a series of standard synthetic methods understood by those skilled in the art. These additional steps will be understood to include the optional use of standard protecting groups as appropriate.

The nucleophilic substitution reaction involving compound 13 is typically performed in an aprotic solvent at temperatures ranging from ambient temp to 200° C., optionally with microwave heating. Additional conditions for the conversion of 11 to 14 or 12 to 15 include the addition of a base, for example potassium tert-butoxide or sodium hydride. In some embodiments, the conversion of nitro-phenol 12 to ether 15 is performed in the presence of an acid, for example by treatment with HCl while heating in chlorobenzene. In some embodiments, the union of 11 or 12 with 13 is catalyzed by transition metals, for example copper (Ullmann coupling) or palladium (Buchwald-Hartwig coupling). In the instance in which nitrophenol 12 is employed, the intermediate nitro-ether 15 is converted to amine 14 by standard reducing conditions, for example, by hydrogenation, by reduction with zinc metal or by reduction with stannous chloride. In the instance in which the L-moiety of 14 or 15 is different than the W-moiety of 3, the L-moiety is converted to a W-moiety using conditions known to those skilled in the art. Some non-limiting examples of general Scheme 3 are shown in the following Schemes.

Scheme 3

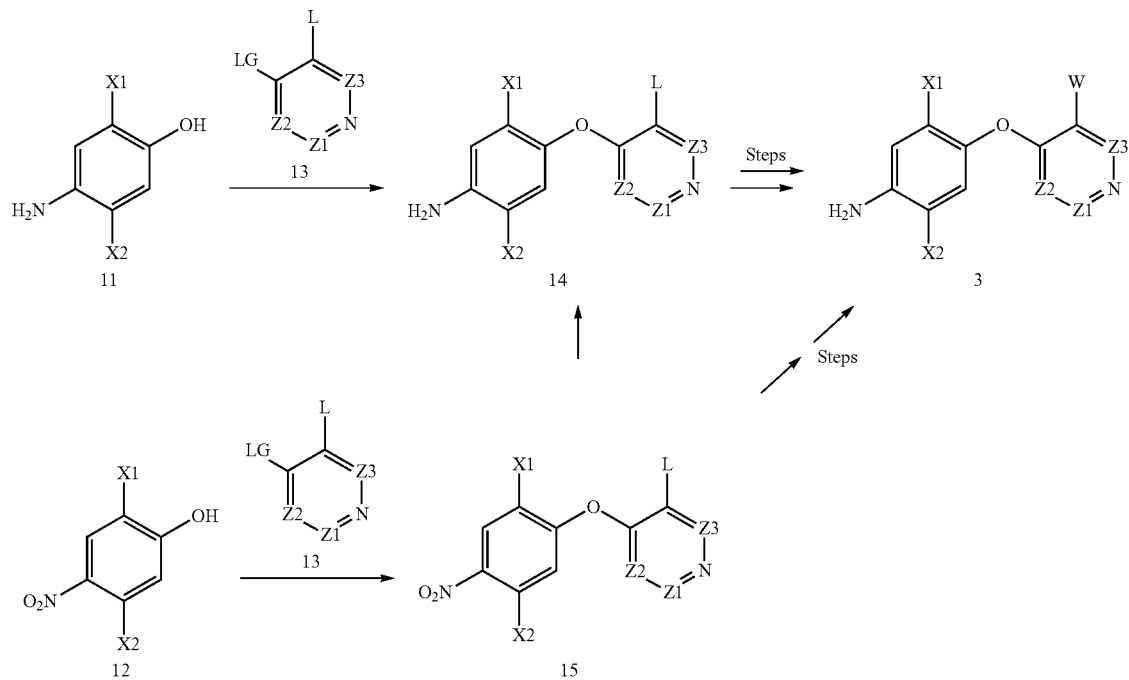

Alternative general syntheses of ethers of formula 15 are shown in Scheme 4. Thus, hydroxy-heteroarenes of formula 17 are reacted with 4-fluoronitrobenzenes 16 to provide ether 15, which in turn is reduced to general amines of formula 14 as described above. Conditions for the union of 16 and 17 include the use of a base, for example cesium carbonate or sodium hydride in a polar aprotic solvent such as dimethylformamide or dimethylsulfoxide with optional heating or microwave heating. Those skilled in the art will recognize that the hydroxy-heteroarene 17 also exists in a tautomeric state found as a pyridone, pyrimidinone, pyridazinone, or triazinone, the tautomeric structures of which are implicitly contained within formula 17. In certain embodiments, ethers of formula 15 can also be prepared by nitration of compounds of formula 19. Ethers of formula 19 are prepared using the conditions of Scheme 3 by the reaction of phenols of formula 18 with pyridine, pyrimidine, pyridazine or triazine of general formula 13.

Scheme 4

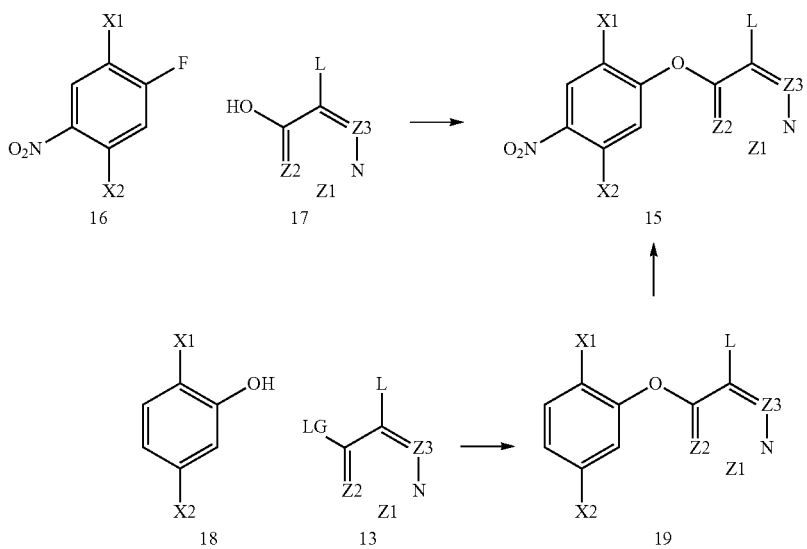

A general method of preparation of general amines 3 from intermediate 14 is illustrated in Scheme 5. Thus, the reaction of compound 14 (prepared according to Scheme 3, L is halogen) with an organometallic reagent M-W (20) in the presence of a palladium catalyst, for example Pd(PPh$_3$)$_4$, provides compounds of formula 3. The M-group of M-W 20 represents a "metallic" functionality known to undergo palladium-catalyzed reactions with aryl halides. Examples of M-groups include boronic acids or esters, trifluoroborates, tin, copper, zinc, magnesium and lithium. These M-W reagents (20), when not commercially available, are generally prepared from analogous halides by methods familiar to those skilled in the art.

Scheme 5

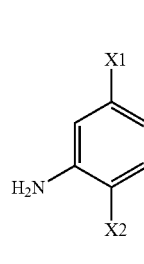

L is halogen

Scheme 6 illustrates the preparation of amine 7 (an example of general amine 3 wherein X1 and X2 are fluoro, Z1 and Z3 are CH, Z2 is N, and W is N-methyl-4-pyrazolyl) using the method of Scheme 3 and Scheme 5. Thus, the amino-phenol 21 (an example of general phenol 11 wherein X1 and X2 are fluoro; see Scheme 3) is reacted with potassium tert-butoxide and pyrimidine 22 (an example of general intermediate 13 wherein Z1 and Z3 are CH, Z2 is N, L is iodo, and LG is chloro; see Scheme 3) to provide iodide 23, an example of general amine 14 wherein L is iodo. Further reaction of iodide 23 with pyrazole boronate 24 (an example of M-W 20 wherein M is 4,4,5,5-tetramethyl-1,3,2-dioxaborolan-2-yl) in the presence of Pd(PPh$_3$)$_4$ provides pyrazole 7, an example of general amine 3 wherein W is N-methyl-4-pyrazolyl.

Scheme 6

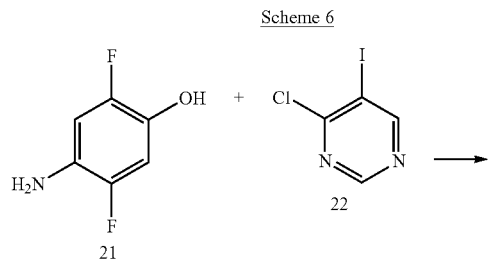

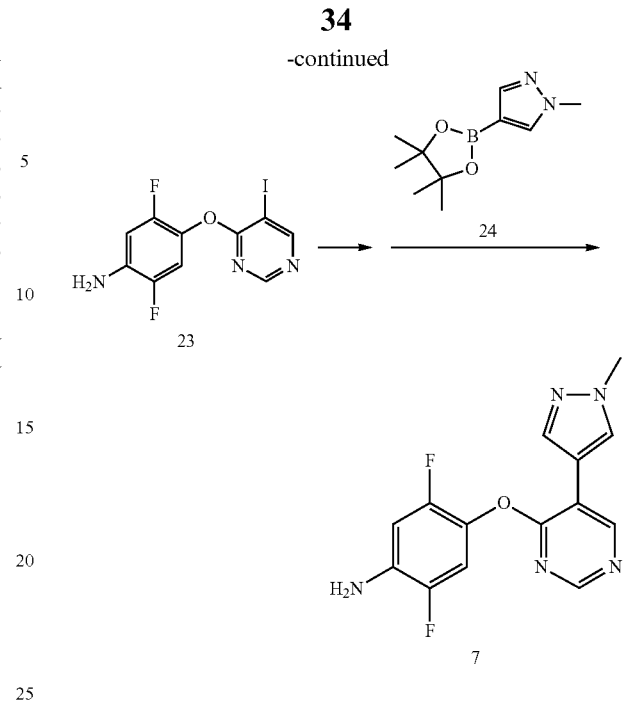

Those skilled in the art will understand that within Scheme 3, the steps leading from intermediates 14 or 15 to general amine 3 also include functional group inter-conversions at any substituted position of intermediates 14 or 15. For example, implicit within Scheme 3 would be the conversion of intermediate 14 wherein Z3 is CCl into general amine 3 wherein Z3 is CR3. A non-limiting example of this is illustrated in Scheme 7 for the preparation of NHR4-substituted amines of general formula 34 and 35. Thus, following the conditions of Scheme 3, the reaction of general nitro-phenol 12 with pyridine 25 (see *Syn. Comm.* (1992), 22, pg. 2829) or pyrimidine 26 (commercially available) provides 27 or 28 respectively. Reduction of the nitro moiety of 27 or 28 as described above provides 29 or 30, examples of general intermediate 14 wherein L is bromo, Z3 is CR3 and R3 is chloro. Further reaction of chloropyridine 29 or chloropyrimidine 30 with general amine NH$_2$—R4 (31) provides 32 or 33, respectively. Further reaction of 32 or 33 with 20, as described above, provides 34 or 35, examples of general amine 3 wherein Z3 is CR3 and R3 is —NHR4.

Scheme 7

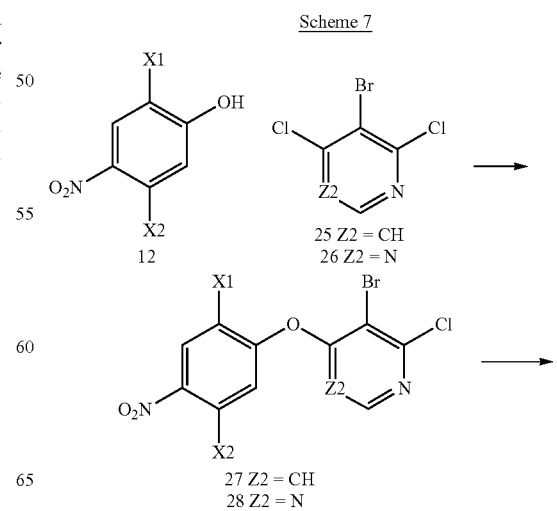

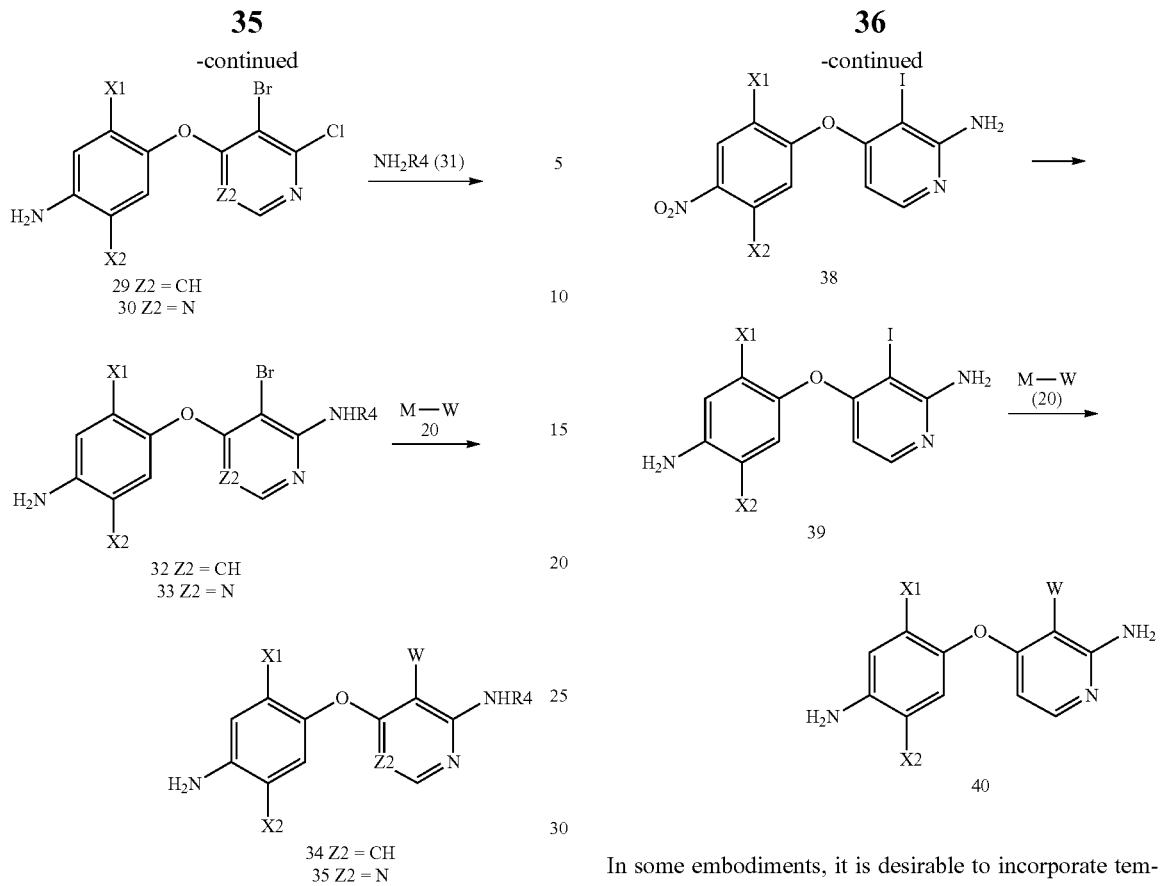

Scheme 8 illustrates an example of general Scheme 4 and Scheme 5. Thus, reaction of the chloropyridine 36 with phenol 18 and a base provides ether 37, an example of general intermediate 19 (wherein L is iodo, Z1, Z2 are CH, Z3 is CR3, R3 is —NHR4, R4 is Nitration of 37 provides the nitro ether 38. Reduction of nitro 38 provides amine 39. Further reaction of 39 with M-W (20) (as described above in Scheme 5) provides amine 40, an example of general amine 3, that is used to prepare compounds of formula 1 (Scheme 1).

Scheme 8

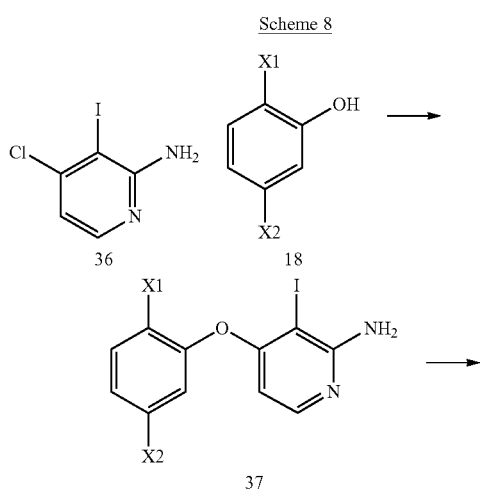

In some embodiments, it is desirable to incorporate temporary protecting groups to mask reactivity of certain functional groups in the course of a synthesis. Thus the reaction arrows in Scheme 1 implicitly represent either a single reaction or a reaction sequence that contains, for example, the removal of a protecting group and/or subsequent inter-conversion of substituents. By way of example, Scheme 9 illustrates a modification of Scheme 1 that provides a library of compounds of formula 1 with differing R5 substituents. Thus, using standard peptide coupling conditions, general acid 2 is coupled with amine 43 to provide 44. Amine 43 is an example of general amine 3 wherein Z1 and Z2 are CH, Z3 is CR3, R3 is bis(tert-butoxycarbonyl)amine. Those skilled in the art will recognize that the tert-butoxycarbonyl (BOC) groups of 43 and 44 are protecting groups that are removed upon exposure to acid. Removal of the BOC protecting groups from 44 by exposure to acid, for example trifluoroacetic acid, provides amino-pyridine 45, an example of compound 1 wherein Z3 is CR3 and R3 is $NH_2$. Further treatment of 45 with a carbonylation reagent (46) provides compounds of formula 47, additional examples of compound 1. In carbonylation reagent 46, in some embodiments the Y-moiety is hydroxyl or halogen. When Y is hydroxyl, reagent 46 is a carboxylic acid that is coupled with amine 45 using standard peptide coupling reagents. When Y is halogen, reagent 46 is an acid halide or a haloformate that will react with amine 45 to provide an amide or carbamate. As indicated in Scheme 9, the requisite amine 43 is readily prepared from aminopyridine 38 by treatment with di-tert-butyl dicarbonate in the presence of a base, for example, triethylamine, to obtain 41. Reduction of the nitro-moiety of 41 affords 42. Further reaction of 42 with M-W (20) (as described above in Scheme 5) provides amine 43.

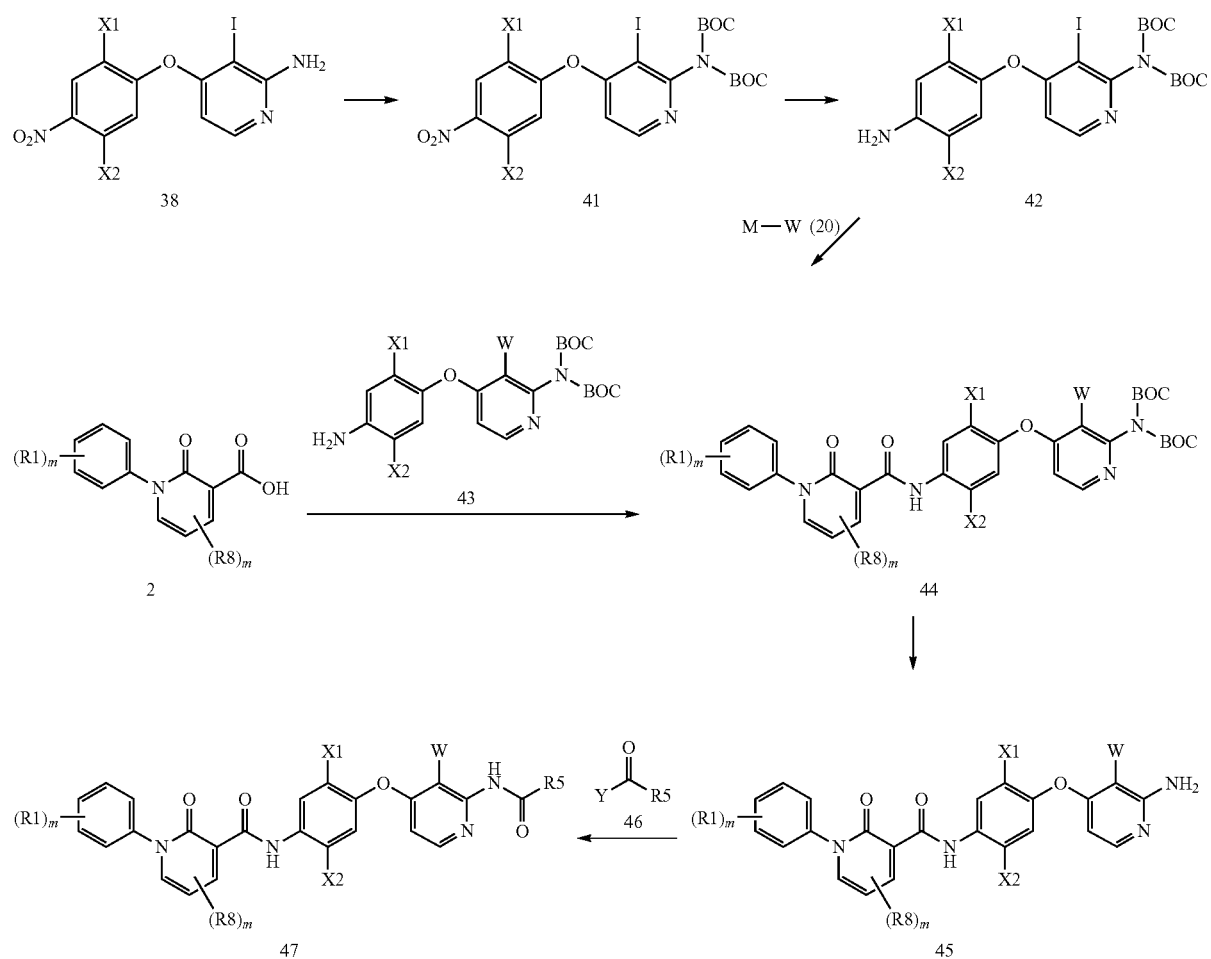

As an extension of Scheme 9, Scheme 10 illustrates the preparation of ureas of formulae 51, 53 and 55. Thus, amine 45 is reacted with 2,2,2-trichlorethyl chloroformate or iso-propenyl chloroformate to provide the activated carbamates 48 or 49 respectively. Further reaction of 48 or 49 with amines of formula 50 provide ureas of formula 51, additional examples of compound 1. Similarly, reaction of 48 or 49 with heterocyclic amines of formula 52 (for example, morpholine, pyrrolidine, piperidine, piperazine) provides ureas of formula 53. Additionally, reaction of 45 with isocyanates (54) directly provides ureas of formula 55.

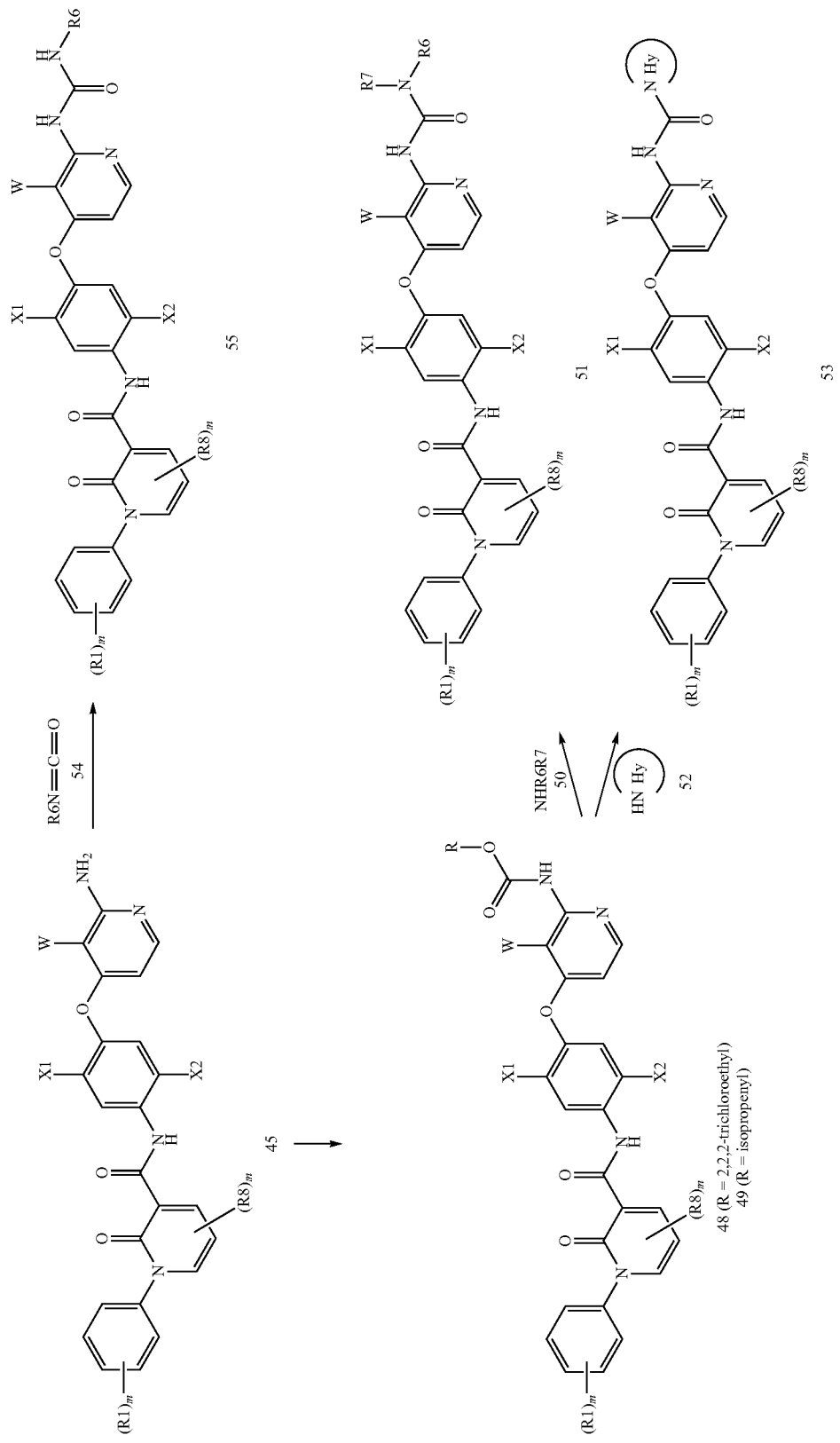

In a manner similar to Scheme 7 and Scheme 8, Scheme 11 illustrates the preparation of amine 60, an additional example of general amine 3. Thus intermediate 56 is reacted with compounds of formula R4-X (57), wherein X is a leaving group such as halide or sulfonate, to provide R4-substituted compounds of formula 58. Reduction of the nitro group of 58 provides 59. In turn, iodide 59 is subjected to a palladium mediated coupling with 20 to provide 60, an additional example of general amine 3.

General acids 2 are prepared from pyranones of formula 61 by the sequence shown in Scheme 12. Thus, treatment of 61 (R is alkyl) with aniline 62 followed by cyclodehydration of the initial adduct (not shown) provides N-aryl pyridine esters of formula 63. Subsequent hydrolysis of 63 provides acid 2. Alternately, ester 63 is available from the reaction of NH pyridone 64 (R is alkyl) with aryl iodide 65 in the presence of a copper catalyst. Conditions for this latter transformation include heating between 50° C. and 200° C. in the presence of copper iodide and optionally in the presence of a ligand, for example 8-hydroxyquinoline. Additionally, pyridones 63 are prepared from acyclic starting material 66 (wherein R is alkyl). The LG group of 66 is a leaving group, for example an alkoxy, dialkylamino or halo moiety. The R8 moieties in 66 are independently variable, such that they are the same or different from one another. In some embodiments, R8 is hydrogen. Reaction of with aniline 62 provides 67. Further treatment of 67 with a base, for example sodium hydride, promotes cyclization to 63.

Scheme 13 illustrates the preparation of acids 71 and 74, examples of general acid 5. Using methods described in *J. Med. Chem.* (2008) 51, pp 5330-5341, Meldrum's acid (68) and acid chloride 69 are combined to yield pyridone ester 70. When not commercially available, acid chlorides 69 are readily prepared from the corresponding acids by treatment with thionyl chloride. Saponification of ester 70 provides acid 71, an example of general amine 5. Further treatment of 70 with alkyl halide 72 in the presence of a base, for example potassium carbonate, provides the R8-substituted pyridone ester 73. Saponification of ester 73 affords acid 74, a further example of general acid 5.

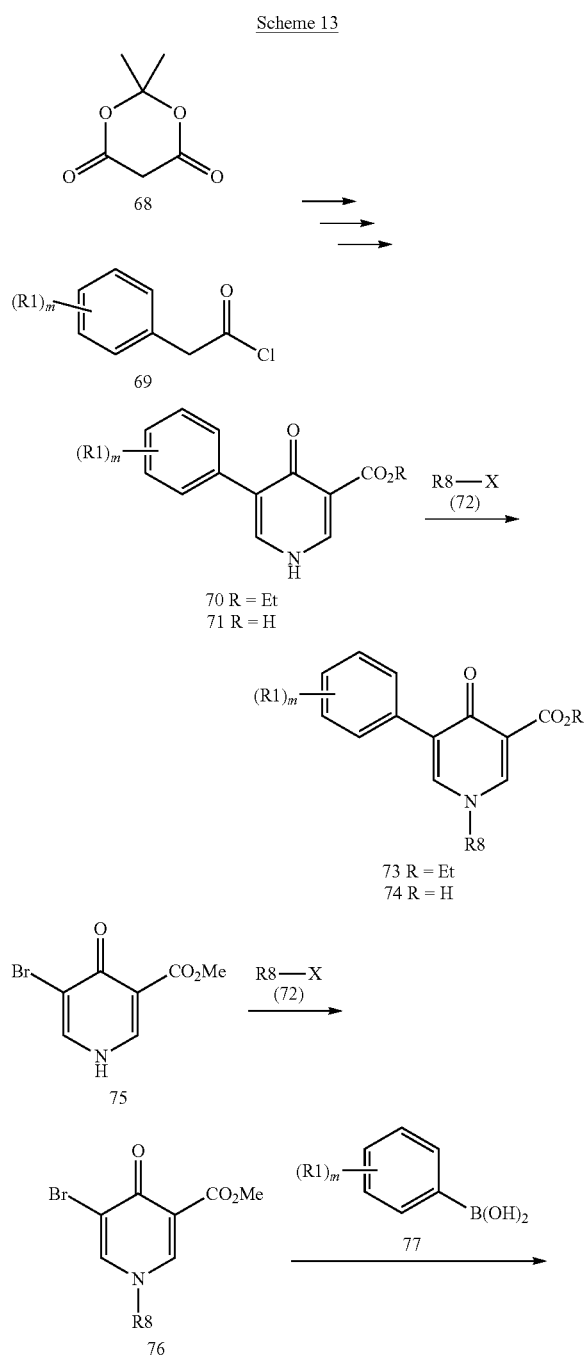

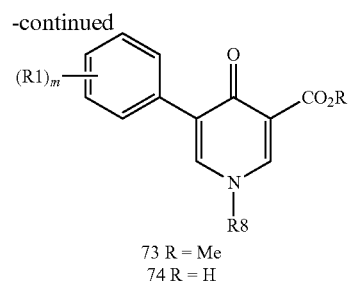

An additional synthesis of acid 74 is also illustrated in Scheme 13 commencing with bromide 75 (see *J. Med. Chem.* (2008) 51, pp 5330-5341). Thus, alkylation of 75 with 72, as described above, provides 76. Treatment of 76 with boronic acid 77 (or analogous boronates, not shown) in the presence of a palladium catalyst and a carbonate base provides pyridine ester 73. Saponification of ester 73 provides acid 74.

A variation to the synthesis of 4-pyridones of formula 4 is shown in Scheme 14 for the preparation of 81. Thus, treatment of pyrone acid halide 78 (prepared by the general methods of *J. Med. Chem.* (2008) 51, pp 5330-5341) with general amine 3 provides pyrone 79. Further treatment of 79 with R8-substituted amines (80) provides pyridones 81.

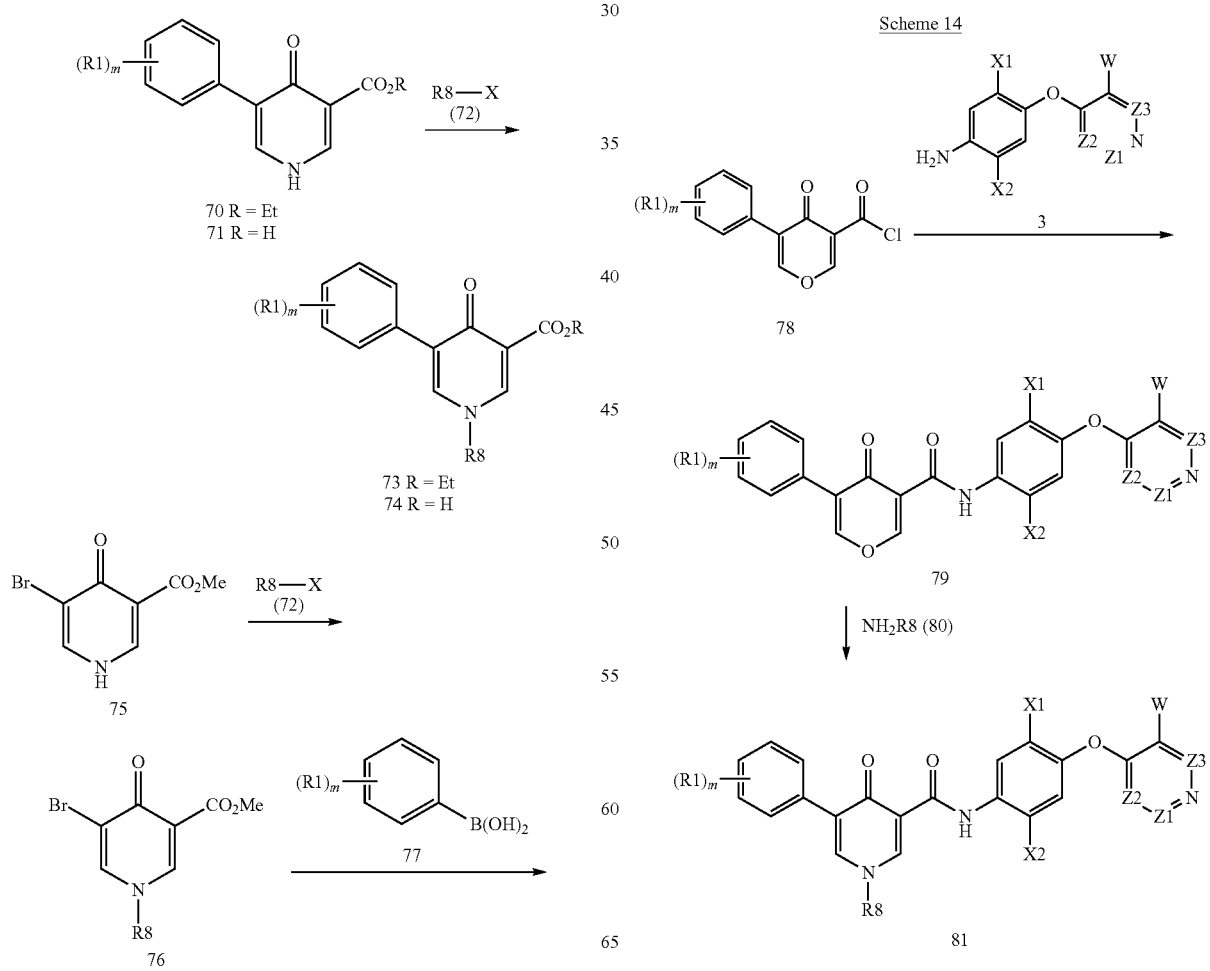

In a manner related to Scheme 12, Scheme 15 illustrates a further preparation of 2-pyridone acids and amides of the invention. Using the methods of *J. Med. Chem.* (2009) 52, pp 1251-1254, methoxy pyridine 82 is first demethylated by treatment with iodotrimethylsilane. The resultant species is then reacted with boronic acid 77 in the presence of copper(II) acetate, to provide N-aryl pyridone 83. Oxidation of the aldehyde to the carboxylic acid 84 is then followed by conversion to the acid chloride (85) by treatment with thionyl chloride. Reaction of 85 with general amine 3 affords 86. Finally, replacement of the iodide with another R8 moiety by reaction of 86 with 87 provides compound 88, an example of formula 1. In the instance in which R8 is an alkoxy moiety, reagent 87 represents an alcohol (wherein M is H) or an alkoxide (wherein M is alkali) that displaces the iodide to form a carbon-oxygen bond. In the instance in which R8 is cyano, reagent 87 represents a metal cyanide (wherein M is Cu or Zn) that replaces the iodine atom of 86, in some embodiments in the presence of a transition metal, for example palladium. In the instance in which R8 is alkyl, the "M" moiety of 87 represents a "metallic" functionality known to undergo palladium-catalyzed reactions with aryl halides. Examples of M-groups include boronic acids or esters, trifluoroborates, tin, copper, zinc, magnesium and lithium. Those skilled in the art will recognize that in certain instances, an alkyl R8 is introduced as a vinylic or acetylenic moiety that is subsequently converted to an alkyl moiety by standard reducing conditions such as hydrogenation over a transition metal catalyst.

Scheme 15

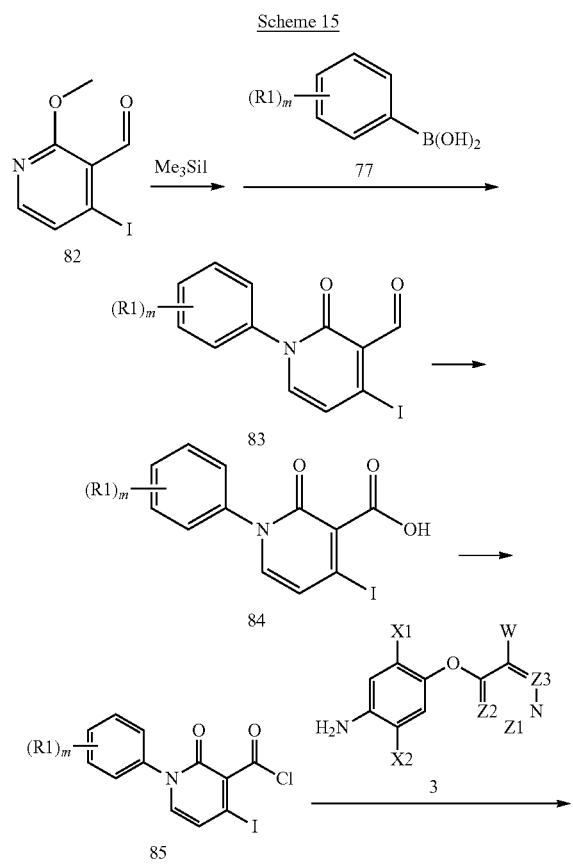

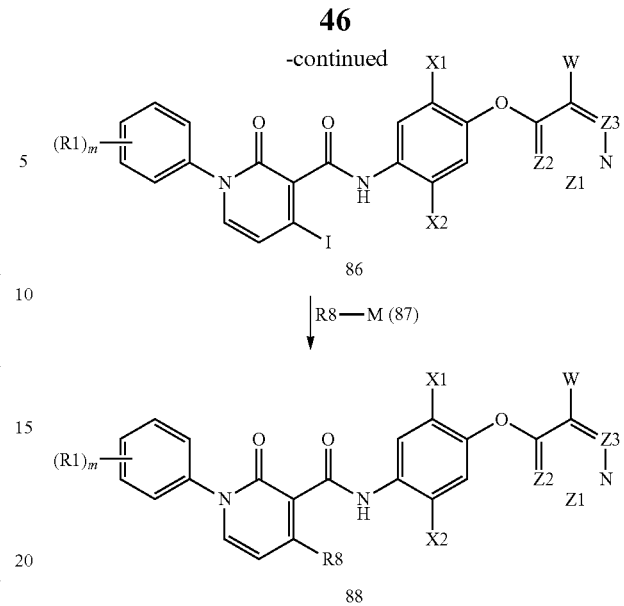

Using the synthetic procedures and methods described herein and methods known to those skilled in the art, the following compounds were made: N-(2,5-difluoro-4-(5-(1-methyl-1H-pyrazol-4-yl)pyrimidin-4-yloxy)phenyl)-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-1-(4-fluorophenyl)-2-oxo-1,2-dihydropyridine-3-carboxamide, N-(4-(3-(1-(cyanomethyl)-1H-pyrazol-4-yl)pyridin-4-yloxy)-2,5-difluorophenyl)-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(4-(2-amino-3-(1-methyl-1H-pyrazol-4-yl)pyridin-4-yloxy)-2,5-difluorophenyl)-1-(4-fluorophenyl)-2-oxo-1,2-dihydropyridine-3-carboxamide, N-(5-chloro-2-fluoro-4-(3-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-5-(4-fluorophenyl)-1-methyl-4-oxo-1,4-dihydropyridine-3-carboxamide, N-(4-(2-amino-3-(1-methyl-1H-pyrazol-4-yl)pyridin-4-yloxy)-2,5-difluorophenyl)-4-ethoxy-1-(4-fluorophenyl)-2-oxo-1,2-dihydropyridine-3-carboxamide, N-(4-(3-(1H-pyrazol-4-yl)pyridin-4-yloxy)-2,5-difluorophenyl)-4-ethoxy-1-(4-fluorophenyl)-2-oxo-1,2-dihydropyridine-3-carboxamide, N-(4-(2-amino-3-(1-methyl-1H-pyrazol-4-yl)pyridin-4-yloxy)-2,5-difluorophenyl)-5-(4-fluorophenyl)-1-methyl-4-oxo-1,4-dihydropyridine-3-carboxamide.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example A1

To a solution of 4-amino-2,5-difluorophenol (0.190 g, 1.310 mmol) in DMF (10 mL) was added potassium tert-butoxide (0.168 g, 1.497 mmol). The mixture was stirred at RT for 30 min. 4-Chloro-5-iodopyrimidine (0.30 g, 1.248 mmol) was added and the reaction mixture was heated at 80° C. overnight. The reaction mixture was quenched with water and the solution was extracted with EtOAc (3×). The organic solution was washed with 5% aqueous lithium chloride solution and brine. The organics were dried over $MgSO_4$, filtered, and concentrated. The crude was purified by silica gel column chromatography (10% to 50% EtOAc/hexane) to obtain 2,5-difluoro-4-(5-iodopyrimidin-4-yloxy)benzenamine (160 mg, 36.7% yield) which was used for the next reaction. MS (ESI) m/z: 349.9 ($M+H^+$).

To a degassed solution of 2,5-difluoro-4-(5-iodopyrimidin-4-yloxy)benzenamine (0.23 g, 0.659 mmol) in DMF (5 mL) was added 1-methyl-pyrazole-4-boronic acid pinacol ester (0.206 g, 0.988 mmol), cesium carbonate (0.644 g, 1977 mmol) in water (2 mL) and $Pd(PPh_3)_4$ (0.076 g, 0.066 mmol) and the mixture was stirred at 80° C. under an argon atmosphere for 1 hour. Water was added and the solution was extracted with EtOAc (3×). The organics were washed with 5% aqueous lithium chloride solution and brine, and then dried over $MgSO_4$. The organics were filtered and concentrated under reduced pressure. The residue was treated with small amount of EtOAc and $Et_2O$. The solid was collected by filtration to obtain 2,5-difluoro-4-(5-(1-methyl-1H-pyrazol-4-yl)pyrimidin-4-yloxy)benzenamine (0.18 g, 90% yield). $^1$H NMR (400 MHz, DMSO-$d_6$): δ 9.02 (s, 1H), 8.54 (s, 1H), 8.30 (s, 1H), 8.09 (s, 1H), 7.21 (m, 1H), 6.69 (m, 1H), 5.42 (s, 2H), 3.89 (s, 3H); MS (ESI) m/z: 304.1 ($M+H^+$).

Example A2

2,5-Difluoro-4-nitro-phenol (1.739 g, 9.93 mmol) and 3-bromo-4-chloro-pyridine (0.637 g, 3.31 mmol) were dissolved in chlorobenzene (6 mL) and heated at 145° C. overnight. The solvent was removed under reduced pressure and the residue partitioned between EtOAc and 10% aqueous $K_2CO_3$. The mixture was extracted with EtOAc (2×), and the combined organic extracts were washed with 10% aqueous $K_2CO_3$ and brine, dried, evaporated and purified by silica gel chromatography (hexanes/EtOAc) to yield 3-bromo-4-(2,5-difluoro-4-nitrophenoxy)pyridine (414 mg, 38% yield). $^1$H NMR (400 MHz, DMSO-$d_6$): δ 8.84 (s, 1H), 8.51-8.45 (m, 2H), 7.82-7.78 (m, 1H), 7.22 (d, 1H); MS (ESI) m/z: 331.0 ($M+H^+$).

3-Bromo-4-(2,5-difluoro-4-nitrophenoxy)pyridine (0.414 g, 1.25 mmol) was dissolved in EtOH (30 mL). Tin (II) chloride dihydrate (1.129 g, 5.00 mmol) was added and the mixture was heated at 80° C. for 4 h. The solvent was removed under reduced pressure and the residue quenched with saturated aqueous $NaHCO_3$. The mixture was diluted with EtOAc and filtered through Celite®. The Celite® bed was washed with water (2×) and EtOAc (2×), and the filtrate was extracted with EtOAc (2×). The combined organic extracts were dried and evaporated to yield 4-(3-bromopyridin-4-yloxy)-2,5-difluorobenzenamine (0.42 g, 112% yield). $^1$H NMR (400 MHz, DMSO-$d_6$): δ 8.68 (s, 1H), 8.33 (d, 1H), 7.28-7.23 (m, 1H), 6.76-6.71 (m, 2H), 5.56 (br s, 2H); MS (ESI) m/z: 301.0 ($M+H^+$).

Example A3

In a sealed tube, 4-(3-bromopyridin-4-yloxy)-2,5-difluorobenzenamine (0.42 g, 1.395 mmol), 1-methyl-4-(4,4,5,5-tetramethyl-1,3,2-dioxaborolan-2-yl)-1H-pyrazole (0.363 g, 1.744 mmol), potassium carbonate (0.578 g, 4.18 mmol), and tetrakistriphenylphosphine palladium (0) (0.081 g, 0.070 mmol) were suspended in dioxane (8 mL) and water (1.333 mL). The mixture was degassed with Ar and heated at 90° C. overnight. The reaction mixture was cooled and partitioned between EtOAc and saturated aqueous $NaHCO_3$. The mixture was extracted with EtOAc (3×). The combined organic extracts were dried, evaporated and purified by silica gel chromatography (hexanes/EtOAc) to yield 2,5-difluoro-4-(3-(1-methyl-1H-pyrazol-4-yl)pyridin-4-yloxy)benzenamine (272 mg, 65% yield). $^1$H NMR (400 MHz, DMSO-$d_6$): δ 8.80 (s, 1H) 8.22-8.20 (m, 2H), 8.00 (s, 1H), 7.24-7.19 (tri, 1H), 6.76-6.71 (m, 1H), 6.62 (d, 1H), 5.50 (br s, 2H), 3.78 (s, 3H); MS (ESI) m/z: 301.0 ($M+H^+$).

Example A4

To a solution of 4-chloropyridin-2-amine (4.00 g, 31.1 mmol) in THF (60 mL) was added lithium bis(trimethylsilyl) amide in THF (1.0 M, 65.3 ml, 65.3 mmol) at −5° C. under Ar atmosphere. After 10 minutes, di-tert-butyl dicarbonate was added (7.22 ml, 31.1 mmol) and stirring was continued for 1 h. Sat. $NH_4Cl$ solution (70 mL) was added and layers were separated. The aqueous layer was extracted with EtOAc (30 mL) and the combined organics were washed with brine, dried ($Na_2SO_4$) and concentrated to afford crude product, which was stirred with 30% EtOAc-hexanes (50 mL) for 5 min. The resultant suspension was filtered, washed with 30% EtOAc-hexane (2×5 mL) and dried to afford tert-butyl (4-chloropyridin-2-yl)carbamate as a white solid (5.5 g, 77% yield).

A solution of tert-butyl (4-chloropyridin-2-yl)carbamate (5.5 g, 24.05 mmol) and N,N,N',N'-tetramethylethylenediamine (7.26 mL, 48.1 mmol) in THF (100 mL) was cooled to −78° C. and treated with n-BuLi (2.5 M in hexanes, 19.24 mL, 48.1 mmol) drop wise over a period of 20 minutes. The mixture was stirred at the same temperature for 1 h. A solution of iodine (12.21 g, 48.1 mmol) in THF (40 mL) was added and stirring was continued at −78° C. for 30 min and at ambient temp of 1 h. Sat. aq $NH_4Cl$ solution (80 mL) was added and the layers were separated. The aqueous layer was extracted with EtOAc (50 mL) and the combined organics were washed with 10% aq. $Na_2S_2O_3$ solution (40 mL) and brine. The extracts were dried ($Na_2SO_4$) and concentrated to dryness. A solution of 30% EtOAc-hexanes (30 mL) was added and the mixture was sonicated for 10 min. The resultant precipitate was collected by filtration, washed with 30% EtOAc-hexanes and dried in vacuo to afford tert-butyl (4-chloro-3-iodopyridin-2-yl)carbamate as off-white solid (5.6 g, 65% yield). $^1$H NMR (400 MHz, DMSO-$d_6$): δ 9.45 (s, 1H); 8.28 (d, J=5.6 Hz, 1H); 7.46 (d, J=5.6 Hz, 1H); 1.43 (s, 9H).

A solution of aqueous HBr (48%, 10 mL, 13.26 mmol) was added to tert-butyl (4-chloro-3-iodopyridin-2-yl)carbamate (4.7 g, 13.26 mmol) and the suspension was stirred at RT for 3 h. The reaction mixture was diluted with water (40 ml), basified with 2N NaOH and the resultant suspension was filtered, washed with water (4×1 mL) and dried to afford 4-chloro-3-iodopyridin-2-amine as white solid (3.05 g, 90% yield). MS (ESI) m/z: 254.9 ($M+H^+$).

4-chloro-3-iodopyridin-2-amine (3.00 g, 11.79 mmol), 2,5-difluoro phenol (4.60 g, 35.4 mmol), DBU (1.777 ml, 11.79 mmol) were combined in NMP (15 mL) and solution was stirred at 170° C. for 6 h under microwave irradiation. The crude reaction mixture was poured into 1N NaOH solution (70 mL), the resultant suspension was filtered, washed with water (5×10 mL) and dried to afford crude product which was purified by silica gel chromatography (EtOAc-hexanes) to afford 4-(2,5-difluorophenoxy)-3-iodopyridin-2-amine as white solid. (2.55 g, 62.1% yield). $^1$H NMR (400 MHz, DMSO-$d_6$): δ 7.74 (d, J=7.6 Hz, 1H), 7.47 (m, 1H), 7.28 (m, 1H), 7.18 (On, 1H), 6.25 (br s, 2H), 5.88 (dd, J=5.6 Hz, 1H); MS (ESI) m/z: 349.03 (M+H$^+$).

A chilled (−10° C.) mixture of 4-(2,5-difluorophenoxy)-3-iodopyridin-2-amine (2.31 g, 6.64 mmol) in sulfuric acid (15 ml) was treated with nitric acid (0.35 ml, 7.96 mmol) while maintaining the temperature below 0° C. After stirring for 20 minutes, the mixture was poured into ice-cold 2 N aq. NaOH solution (100 mL of 2 N NaOH in ice) with stirring. The pH of the resultant solution was then made basic by careful addition or NaHCO$_3$. After stirring for 30 min, the suspension was filtered, washed with water (3×10 mL) and dried to afford 4-(2,5-difluoro-4-nitrophenoxy)-3-iodopyridin-2-amine as light red solid (2.05 g, 79% yield). MS (ESI) m/z: 393.9 (M+H+).

To a solution of 4-(2,5-difluoro-4-nitrophenoxy)-3-iodopyridin-2-amine (0.78 g, 1.78 mmol) in EtOH (15 mL) added tin(II) chloride dihydrate (2.0 g, 8.93 mmol) and the reaction mixture was stirred at 80° C. for 3 h. The mixture was cooled to RT, the solvent was removed in vacuo and crude residue was basified with NaHCO$_3$ solution (40 mL). EtOAc (50 mL) was added to the resultant white suspension and the mixture was stirred for few minutes. It was filtered though a Celite® pad which was washed with EtOAc (4×5 mL), and water (3×4 mL). The organic layer was separated and was washed with brine, dried (Na$_2$SO$_4$) and concentrated to afford crude product which was purified by silica gel chromatography (EtOAc-hexanes) to afford 4-(4-amino-2,5-difluorophenoxy)-3-iodopyridin-2-amine as an off-white solid (0.33 g, 51% yield). $^1$H NMR (400 MHz, DMSO-$d_6$): δ 7.69 (d, J=5.6 Hz, 1H), 7.12 (dd, J=11.2 Hz, 7.6 Hz, 1H), 6.69 (dd, J=12.0 Hz, 8.0 Hz, 1H), 6.13 (s, 2H), 5.74 (d, J=5.6 Hz, 1H), 5.47 (s, 2H); MS (ESI) m/z: 364.0 (M+H$^+$).

To a degassed solution of 4-(4-amino-2,5-difluorophenoxy)-3-iodopyridin-2-amine (0.33 g, 0.91 mmol), 1-methyl-4-(4,4,5,5-tetramethyl-1,3,2-dioxaborolan-2-yl)-1H-pyrazole (0.28 g, 1.36 mmol) in dioxane (5 ml) was added a degassed solution of K$_2$CO$_3$ (0.37 g, 2.73 mmol) in water (2 mL) and tetrakis(triphenylphosphine)palladium(0) (0.105 g, 0.09 mmol). The resultant mixture was stirred for 16 h at 90° C. Sat. NaHCO$_3$ solution (35 mL) was added. The resultant mixture was extracted with EtOAc (2×30 mL). The combined organics were washed with brine, dried (Na$_2$SO$_4$) and concentrated in vacuo. The residue was purified by silica gel chromatography (MeOH/CH$_2$Cl$_2$) to afford 4-(4-amino-2,5-difluorophenoxy)-3-(1-methyl-1H-pyrazol-4-yl)pyridin-2-amine (188 mg, 65.2%) as white solid (188 mg, 65.2% yield). $^1$H NMR (400 MHz, DMSO-$d_6$): δ 7.85 (s, 1H), 7.70 (d, J=6.0 Hz, 1H), 7.57 (s, 1H), 7.06 (dd, J=11.2 Hz, 7.2 Hz, 1H), 6.66 (dd, J=12.0 Hz, 8.0 Hz, 1H), 5.86 (d, J=5.6 Hz, 1H), 5.60 (s, 2H), 5.39 (s, 2H), 3.85 (s, 3H); MS (ESI) m/z: 318.1 (M+H$^+$).

Example A5

A mixture of 2-chloro-5-fluorophenol (1.50 g, 10.24 mmol), 3-bromo-4-chloropyridine (1.50 g, 7.79 mmol) and DBU (1.50 g, 9.85 mmol) were heated at 130° C. in NMP (10 mL) for 15 hours. The reaction mixture was cooled and partitioned between water (100 mL) and MTBE (100 mL). The organic layer was separated, washed with dilute aq NaOH and brine, dried (MgSO$_4$) and concentrated in vacuo to provide 3-bromo-4-(2-chloro-5-fluorophenoxy)pyridine (1.98 g, 84% yield) as brownish oil suitable for use in the next reaction. MS (ESI) m/z: 303.9 (M+H$^+$).

To a cold (−10° C.) solution of 3-bromo-4-(2-chloro-5-fluorophenoxy)pyridine (1.98 g, 6.54 mmol) in conc. sulfuric acid (5 ml) was added nitric acid (0.55 ml, 8.69 mmol). The resultant mixture was stirred at the same temp for 20 minutes and was then allowed to warm to ambient temp for 30 min. The reaction mixture was treated with crushed ice, stirred, filtered, washed and dried to provide 3-bromo-4-(2-chloro-5-fluoro-4-nitrophenoxy)pyridine, (2.08 g, 91% yield) as orange yellow solid. $^1$H NMR (400 MHz, DMSO-$d_6$) δ 9.00 (s, 1H), 8.62 (m, 2H), 7.81 (d, J=8 Hz, 1H), 7.23 (d, J=2.5 Hz, 1H); MS (ESI) m/z: 348.9 (M+1H$^+$).

To a solution of 3-bromo-4-(2-chloro-5-fluoro-4-nitrophenoxy)pyridine (2.00 g, 5.75 mmol) in ethanol/water (9:1, 50 mL) was added iron powder (2.00 g, 35.8 mmol) followed by ammonium chloride (2.00 g, 37.4 mmol). The mixture was heated at 70° C. for 2 h. The reaction mixture was filtered, and the solids were washed with EtOAc. The filtrate was evaporated to dryness. The residue was taken in ethyl acetate and washed with water and dried. The solvent was evaporated to provide 4-(3-bromopyridin-4-yloxy)-5-chloro-2-fluorobenzenamine as light brownish oil (0.98 g, 53.6% yield). MS (ESI) m/z: 317.0/319.0 (M+H$^+$).

To a solution of 4-(3-bromopyridin-4-yloxy)-5-chloro-2-fluorobenzenamine, (0.300 g, 0.945 mmol) in n-butanol (5 mL) was added 1-methyl-4-(4,4,5,5-tetramethyl-1,3,2-dioxaborolan-2-yl)-1H-pyrazole (0.236 g, 1.134 mmol), S-Phos (0.078 g, 0.189 mmol), Pd$_2$(dba)$_3$ (0.087 g, 0.094 mmol) and potassium phosphate (0.602 g, 2.83 mmol). The resulting mixture was degassed and heated in a sealed tube at 100° C. for 20 h. The solvent from the reaction mixture was completely evaporated. The residue was stirred in a mixture of CH$_2$Cl$_2$-MeOH (1:1), filtered, rinsed, dried and subjected to chromatography (50-100% EtOAc-hexanes) to provide 5-chloro-2-fluoro-4-(3-(1-methyl-1H-pyrazol-yl)pyridin-4-yloxy)benzenamine, (0.148 g, 49.1% yield) as white solid. $^1$H NMR (400 MHz, DMSO-$d_6$) δ 8.80 (s, 1H), 8.20 (m, 2H), 8.01 (s, 1H), 7.24 (d, J=8.5 Hz, 1H), 6.95 (d, J=8.5 Hz, 1H), 6.51 (d, J=5.6 Hz, 1H), 5.51 (s, 2H), 3.88 (s, 3H); MS (ESI) m/z: 319.1 (M+H$^+$).

Example A6

4-(2,5-Difluoro-4-nitrophenoxy)-3-iodopyridin-2-amine (2.05 g, 5.22 mmol) (from Example A4), di-tert-butyl dicarbonate (2.66 ml, 11.47 mmol) and Et$_3$N (0.73 ml, 5.22 mmol) were combined in THF (25 mL) and stirred for 3 h at RT. The reaction mixture was concentrated in vacuo and the residue was purified by silica gel chromatography (EtOAc-hexanes) to afford 4-(2,5-difluoro-4-nitrophenoxy)-3-iodo-2-[bis[(1,1-dimethylethoxy)-carbonyl]amino]pyridine as white solid (1.63 g, 52.7% yield). $^1$H NMR (400 MHz, DMSO-$d_6$): δ 8.47 (dd, J=10 Hz, 7.2 Hz, 1H), 8.37 (d, J=5.4 Hz, 1H), 7.67 (dd, J=11.2 Hz, 6.8 Hz, 1H), 7.06 (d, J=5.6 Hz, 1H), 1.34 (s, 181-1); MS (ESI) m/z: 616.1 (M+Na$^+$).

Palladium hydroxide on carbon (0.193 g, 0.275 mmol) (contains 60% water) was added to a solution of 4-(2,5-difluoro-4-nitrophenoxy)-3-iodo-2-[bis[(1,1-dimethylethoxy)-carbonyl]amino]pyridine (1.63 g, 2.75 mmol) in EtOAc (20 mL) and the mixture was hydrogenated (50) psi for 16 h. The completed reaction mixture was filtered through Celite® rinsing forward with EtOAc (2×10 mL). The combined filtrate was concentrated to afford 4-(2,5-difluoro-4-aminophenoxy)-3-iodo-2-[bis[(1,1-dimethylethoxy)carbonyl]amino]pyridine as colorless foam (1.5 g, 97% yield). $^1$H NMR (400 MHz, DMSO-$d_6$): δ 8.21 (dd, J=7.6 Hz, 5.6 Hz, 1H), 7.24 (dd, J=11.0 Hz, 7.4 Hz, 1H), 6.71 (m, 1H), 6.57 (d, J=5.6 Hz, 1H), 5.55 (s, 2H), 1.35 (s, 18H); MS (ESI) m/z: 564.1 (M+H$^+$).

To a degassed solution of 4-(2,5-difluoro-4-aminophenoxy)-3-iodo-2-[bis[(1,1-dimethylethoxy)carbonyl]amino]pyridine (0.7 g, 1.24 mmol), 1-methyl-4-(4,4,5,5-tetramethyl-1,3,2-dioxaborolan-2-yl)-1H-pyrazole (0.52 g, 2.48 mmol) in dioxane (15 mL) was added $K_2CO_3$ (0.51 g, 3.7 mmol) in water (3 mL). Tetrakis (triphenylphosphine)Palladium(0) (0.14 g, 0.12 mmol) was added and the reaction mixture was stirred at 100° C. for 3 h. The mixture was diluted with water (40 mL) and EtOAc (50 mL). The layers were separated, and the aq. layer was extracted with EtOAc (20 mL). The combined organics were washed with brine, dried ($Na_2SO_4$) and concentrated in vacuo. The residue was purified by silica gel chromatography (EtOAc-hexanes) to afford 4-(4-amino-2,5-difluorophenoxy)-3-(1-methyl-1H-pyrazol-4-yl)-2-[bis[(1,1-dimethylethoxy)carbonyl]amino]pyridine as a colorless foam (0.52 g, 81% yield). $^1$H NMR (400 MHz, DMSO-$d_6$): δ 8.17 (d, J=5.6 Hz, 1H), 7.84 (s, 1H), 7.48 (d, J=0.8 Hz, 1H), 7.21 (dd, J=11.2 Hz, 7.6 Hz, 1H), 6.70 (m, 2H), 5.50 (s, 2H), 3.86 (s, 3H), 1.25 (s, 18H); MS (ESI) m/z: 518.3 (M+H$^+$).

Example B1

To a solution of 4-fluoroaniline (6.5 g, 58.4 mmol) in DMF (30 mL) at ice bath temperature was added methyl 2-oxo-2H-pyran-3-carboxylate (9.0 g, 58.4 mmol). The resulting mixture was stirred for 15 min cold and was then warmed to ambient temp for 3 hours. N-(3-Dimethylaminopropyl)-N'-ethylcarbodiimide hydrochloride (EDCI—HCl) (13.5 g, 70.0 mmol) and DMAP (1.43 g, 11.7 mmol) were added and the resulting mixture was stirred at ambient temp overnight. The reaction mixture was poured into water (300 mL), extracted with ethyl acetate (3×100 mL), washed with brine, dried over anhydrous $Na_2SO_4$ and concentrated in vacuo to obtain methyl 1-(4-fluorophenyl)-2-oxo-1,2-dihydropyridine-3-carboxylate. This crude product was used for the next step without further purification.

A mixture of methyl 1-(4-fluorophenyl)-2-oxo-1,2-dihydropyridine-3-carboxylate (14 g, 58.4 mmol) and 2N aqueous NaOH (90 mL) in methanol (150 mL) was heated at 65° C. overnight. The cooled reaction mixture was treated with 2N HCl solution with stirring until pH=1. The precipitate that formed was collected by filtration, washed with water (10 mL), and dried to give 1-(4-fluorophenyl)-2-oxo-1,2-dihydropyridine-3-carboxylic acid (7.0 g, 53% yield). $^1$H-NMR (400 MHz, MeOH-$d_4$): δ 8.58 (dd, J=7.2, 2.0 Hz, 1H), 8.04 (dd, J=6.8, 2.0 Hz, 1H), 7.53 (m, 2H), 7.31 (m, 2H), 6.83 (t, J=7.2 Hz, 1H).

Example B2

A mixture of ethyl 2-cyanoacetate (120 g, 1.06 mol) and triethylorthoacetate (354 g, 2.12 mol) in glacial acetic acid (33 g, 0.53 mol) was stirred at 120-130° C. overnight. The mixture was concentrated under vacuum to provide crude ethyl 2-cyano-3-ethoxybut-2-enoate. The residue was carried into the next reaction without further purification assuming 100% conversion.

A mixture of ethyl 2-cyano-3-ethoxybut-2-enoate (194 g theory, 1.06 mol) and N,N-dimethylformamide dimethyl acetal (160 g, 1.325 mol) was stirred at 70° C. for 2 hours. The mixture was concentrated under high vacuum to provide crude ethyl 2-cyano-5-(dimethylamino)-3-ethoxypenta-2,4-dienoate. The residue was used directly without further purification.

A mixture of ethyl 2-cyano-5-(dimethylamino)-3-ethoxypenta-2,4-dienoate (150 g, 0.63 mol) and HOAc (600 mL) was refluxed overnight. The mixture was concentrated to dryness under high vacuum and the residue treated with water (300 mL). The mixture was extracted with EtOAc (2×250 mL) to remove the impurities. The pH of the aqueous was adjusted with $NaHCO_3$ to pH ~9-10. The mixture was extracted with $CH_2Cl_2$ (3×300 mL). The combined organics were washed with brine, dried over $Na_2SO_4$ and concentrated. The residue was purified by silica gel chromatography to afford ethyl 4-ethoxy-2-oxo-1,2-dihydropyridine-3-carboxylate (90 g, 66.6% yield).

A mixture of ethyl 4-ethoxy-2-oxo-1,2-dihydropyridine-3-carboxylate (60 g, 0.284 mol), 4-fluoro phenylboronic acid (120 g, 0.853 mol), $Cu(AcO)_2$ (113 g, 0.568 mol) and pyridine (88 g, 1.137 mol) in $CH_2Cl_2$ (500 mL) was stirred at ambient temp (~25° C.) for 4 h open to air. The reaction mixture was filtered and the solids were washed with water. The filtrate was extracted with $CH_2Cl_2$ (2×250 mL). The combined organic layers were dried over $Na_2SO_4$ and concentrated to afford ethyl 4-ethoxy-1-(4-fluorophenyl)-2-oxo-1,2-dihydropyridine-3-carboxylate. The product was carried forward without further purification. (77 g, 95% yield).

A mixture of ethyl 4-ethoxy-1-(4-fluorophenyl)-2-oxo-1,2-dihydropyridine-3-carboxylate (60 g, 0.196 mol) and LiOH (30 g, 0.6 mol) in EtOH (200 mL) and water (100 mL) was stirred at ambient temp (~25° C.) for 16 h. The mixture was concentrated to remove EtOH. The residue was diluted with water (300 mL). The mixture was extracted with EtOAc (100 mL) to remove the impurity. The pH was adjusted with 37% HCl to pH<2. The mixture was extracted with EA (3×300 mL). The combined organics were washed with brine, dried over $Na_2SO_4$ and concentrated to remove EtOAc. Petroleum ether (PE) (200 mL) was added. The resultant precipitate was collected by filtration, washed with PE and dried to afford 4-ethoxy-1-(4-fluorophenyl)-2-oxo-1,2-dihydropyridine-3-carboxylic acid. (43 g, 78.9% yield). $^1$H-NMR (400 MHz, DMSO-$d_4$): δ 7.95 (d, J=8.0 Hz, 1H), 7.48 (m, 2H), 7.35 (m, 2H), 6.58 (d, J=7.6 Hz, 1H), 4.28 (q, J=7.2 Hz, 2H), 1.32 (t, J=7.2 Hz, 3H).

Example B3

A mixture of 4-fluorophenylacetyl chloride (4.91 g, 24.3 mmol), 2,2-dimethyl-1,3-dioxane-4,6-dione (3.50 g, 24.3 mmol) and DIEA (5.84 g, 49.8 mmol) in $CH_2Cl_2$ (30 mL) was stirred for 1 h at 0° C. and at ambient temp for 2 h. The solution was diluted with $CH_2Cl_2$ (40 mL) and the organic phase was washed with 0.1 N HCl and brine, dried over $Na_2SO_4$ and evaporated to dryness. The resulting orange solid was suspended in EtOH (100 mL) and refluxed for 2 hours. The solution was evaporated and the resulting orange oil was left in the freezer overnight to give a yellow solid. The crude solid was recrystallized from EtOH to afford ethyl 4-(4-fluorophenyl)-3-oxobutanoate (5.3 g, 86.8% yield).

A mixture of ethyl 4-(4-fluorophenyl)-3-oxobutanoate (5.3 g, 21.1 mmol), and DMF-dimethylacetal (7.53 g, 63.3 mmol) in toluene (50 mL) was heated at reflux with removal of the MeOH for 2 h and was then concentrated under vacuum. The residue in MeOH (50 mL) was treated with $NH_4OAc$ (8.1 g, 105.5 mmol) and the mixture was refluxed for 1.5 h. The precipitate was collected by filtration and successively washed with MeOH, water, and MeOH to give ethyl 5-(4-fluorophenyl)-4-oxo-1,4-dihydropyridine-3-carboxylate (3.3 g, 60% yield). ¹H-NMR (400 MHz, CD₃OD): δ 9.19 (d, J=0.8 Hz, 1H), 8.81 (d, J=0.8 Hz, 1H), 7.74 (dd, J=8.8, 5.2 Hz, 2H), 7.29 (t, J=8.8 Hz, 2H), 4.60 (q, J=7.2 Hz, 2H), 1.49 (t, J=7.2 Hz, 3H) [NH not visible].

A mixture of ethyl 5-(4-fluorophenyl)-4-oxo-1,4-dihydropyridine-3-carboxylate (1.5 g, 5.7 mmol) and iodomethane (0.9 g, 6.3 mmol) in saturated NaHCO₃ (25 mL) was stirred at 60° C. overnight. The mixture was filtered. The solid was concentrated under vacuum to afford ethyl 5-(4-fluorophenyl)-1-methyl-4-oxo-1,4-dihydropyridine-3-carboxylate (1.1 g, 69.9% yield). The mixture was used directly without further purification.

A mixture of ethyl 5-(4-fluorophenyl)-1-methyl-4-oxo-1,4-dihydropyridine-3-carboxylate (1.1 g, 4 mmol) and NaOH (1.6 g, 40 mmol) in water (25 mL) was stirred at RT overnight. The mixture was extracted with EtOAc (2×25 mL) to remove impurities. The aqueous pH was adjusted to pH 1-2 with 37% HCl. The resulting precipitate was collected by filtration and dried under vacuum to afford 5-(4-fluorophenyl)-1-methyl-4-oxo-1,4-dihydropyridine-3-carboxylic acid (810 mg, 81.9% yield). ¹H-NMR (400 MHz, CDCl₃): δ 15.76 (s, 1H), 8.49 (d, J=2.4 Hz, 1H), 7.58 (m, 3H), 7.14 (t, J=8.8 Hz, 2H), 3.92 (s, 3H).

Example 1

To a solution of Example A1 (0.030 g, 0.10 mmol) in CH₃CN (1 mL) and DMF (1 mL) was added Example B1 (0.028 g, 0.12 mmol) and TBTU (0.035 g, 0.11 mmol). The solution was cooled to 0° C. and then DIEA (0.059 mL, 0.36 mmol) was added. The mixture was allowed to warm to RT with stirring. After 5 hours, addition Example B1 (15 mg) and TBTU (17 mg) were added and the mixture was stirred at RT overnight. The reaction mixture was treated with EtOAc and the resultant solid was filtered, washed with EtOAc and dried under vacuum to obtain N-(2,5-difluoro-4-(5-(1-methyl-1H-pyrazol-4-yl)pyrimidin-4-yloxy)phenyl)-1-(4-fluorophenyl)-2-oxo-1,2-dihydropyridine-3-carboxamide (35 mg, 68.2% yield). ¹H NMR (400 MHz, DMSO-d₆): δ 12.4 (brs, 1H), 9.08 (s, 1H), 8.60 (m, 1H), 8.58 (s, 1H), 8.50 (m, 1H), 8.35 (s, 1H), 8.15 (m, 1H), 8.12 (s, 1H), 7.67 (m, 1H), 7.59 (m, 2H), 7.41 (t, J=8.8 Hz, 2H), 6.74 (t, J=6.8 Hz, 1H), 3.90 (s, 3H); MS (ESI) m/z: 519.2 (M+H⁺).

Example 2

TBTU (0.097 g, 0.301 mmol) was added to a solution of Example B1 (0.070 g, 0.301 mmol), Example A3 (0.07 g, 0.232 mmol), and DIEA (0.081 mL, 0.463 mmol) in DMF (4 mL). The mixture was stirred at room temperature for 8 h. Additional TBTU (0.097 g, 0.301 mmol) and Example B1 (0.070 g, 0.301 mmol) were added and the mixture was stirred overnight at ambient temperature. The reaction mixture was diluted with EtOAc (4 mL) and the precipitate was filtered off and washed with EtOAc. The precipitate was dried under vacuum to yield N-(2,5-difluoro-4-(3-(1-methyl-1,1-pyrazol-4-yl)pyridin-4-yloxy)phenyl)-1-(4-fluorophenyl)-2-oxo-1,2-dihydropyridine-3-carboxamide (97 mg, 81%). ¹H NMR (400 MHz, DMSO-d₆): δ 12.43 (br s, 1H), 8.85 (s, 1H), 8.62-8.53 (m, 2H), 8.25 (s, 1H), 8.24 (s, 1H), 8.15 (d, 1H), 8.01 (s, 1H), 7.65-7.58 (m, 3H), 7.43-7.39 (m, 2H), 6.77-6.72 (m, 2H), 3.88 (s, 3H); MS (ESI) m/z: 518.2 (M+H⁺).

Example 3

A mixture of 4-(4,4,5,5-tetramethyl-1,3,2-dioxaborolan-2-yl)-1H-pyrazole (0.50 g, 2.58 mmol), sodium iodide (39 mg, 0.26 mmol) bromoacetonitrile (1.3 g, 10.8 mmol) and potassium carbonate (1.0 g, 7.8 mmol) in acetonitrile (10 mL) was heated at 70° C. overnight. Water was added and the solution was extracted with EtOAc (3×). The organic was dried over Na₂SO₄, filtered and concentrated. The residue was purified by silica gel column chromatography (10% to 100% EtOAc/hexane) to obtain 2-(4-(4,4,5,5-tetramethyl-1,3,2-dioxaborolan-2-yl)-1H-pyrazol-1-yl)acetonitrile (0.38 g, 63% yield). MS (ESI) m/z: 234.1 (M+H⁺).

Example B1

(0.116 g, 0.497 mmol) was combined with thionyl chloride (1.089 ml, 14.92 mmol) and the mixture heated to 60° C. for 1.5 hours then cooled to room temperature and concentrated to dryness. The resulting residue was treated with toluene and concentrated to dryness (this process repeated twice more) to afford 125 mg (100%) of 1-(4-fluorophenyl)-2-oxo-1,2-dihydropyridine-3-carbonyl chloride as a pale yellow solid.

A solution of Example A2 (0.100 g, 0.332 mmol) in THF (1 mL) was treated with triethylamine (0.069 ml, 0.498 mmol) and a suspension of 1-(4-fluorophenyl)-2-oxo-1,2-dihydropyridine-3-carbonyl chloride (0.125 g, 0.498 mmol) in THF (2 mL). The mixture was blanketed with argon and stirred overnight at room temperature. The solids were removed via filtration, rinsed with THF and the filtrate was concentrated to dryness. The crude material was purified by silica gel chromatography (10-100% EtOAc/Hex) to afford N-(4-(3-bromopyridin-4-yloxy)-2,5-difluorophenyl)-1-(4-fluorophenyl)-2-oxo-1,2-dihydropyridine-3-carboxamide (122 mg, 71% yield) as a pale yellow solid. ¹H NMR (400 MHz, DMSO-d₆): δ 12.45 (s, 1H); 8.74 (s, 1H); 8.58 (m, 2H); 8.38 (d, J=5.6 Hz, 1H); 8.15 (dd, J=6.6, 2.2 Hz, 1H); 7.67 (dd, J=11.0, 7.3 Hz, 1H); 7.60 (dd, J=8.8, 4.9 Hz, 2H); 7.41 (t, J=8.7 Hz, 2H); 6.89 (d, J=5.6 Hz, 1H); 6.74 (t, J=7.0 Hz, 1H); MS (ESI) m/z: 516.0, 518.0 (M+H⁺).

N-(4-(3-Bromopyridin-4-yloxy)-2,5-difluorophenyl)-1-(4-fluorophenyl)-2-oxo-1,2-dihydropyridine-3-carboxamide (0.119 g, 0.231 mmol) was combined with 2-(4-(4,4,5,5-tetramethyl-1,3,2-dioxaborolan-2-yl)-1H-pyrazol-1-yl)acetonitrile (0.054 g, 0.231 mmol) and potassium carbonate (0.096 g, 0.692 mmol) in dioxane (4 mL) and water (0.667 mL), sparged with argon for several minutes, treated with tetrakis(triphenylphosphine)palladium(0) (0.013 g, 0.012 mmol) and heated to 85° C. overnight. The mixture was cooled to room temperature, treated with saturated NaHCO₃ and extracted with EtOAc (2×). The combined organics were washed with brine, dried over MgSO₄ and concentrated to dryness. The crude material was purified over silica gel (40-100% EtOAc/Hex) to afford N-(4-(3-(1-(cyanomethyl)-1H-pyrazol-4-yl)pyridin-4-yloxy)-2,5-difluorophenyl)-1-(4-Fluorophenyl)-2-oxo-1,2-dihydropyridine-3-carboxamide (30 mg, 24% yield) as an off-white solid. ¹H NMR (400 MHz, DMSO-d₆): δ 12.45 (s, 1H); 8.91 (s, 1H); 8.61 (dd, J=7.4, 2.1 Hz, 1H); 8.55 (m, 1H); 8.44 (s, 1H); 8.29 (d, J=5.7 Hz, 1H); 8.24 (s, 1H); 8.16 (dd, J=6.6, 2.2 Hz, 1H); 7.67 (dd, J=11.0, 7.3 Hz, 1H); 7.60 (dd, J=8.7, 4.9 Hz, 2H); 7.42 (t, J=8.7 Hz, 2H); 6.75 (m, 2H); 5.54 (s, 2H); MS (ESI) m/z: 543.1 (M+H⁺).

Example 4

Thionyl chloride (2 mL) was added to Example B2 (0.077 g, 0.28 mmol) and the resultant solution was stirred at 60° C. for 1 h. Solvent was removed, and residue was dissolved in toluene (2 mL) and concentrated under vacuum. Co-evaporation with toluene was repeated one more time to furnish 4-ethoxy-1-(4-fluorophenyl)-2-oxo-1,2-dihydropyridine-3-carbonyl chloride as white solid. This solid was dissolved in THF (2 mL) and was added to a solution of 2,5-difluoro-4-(3-(1-methyl-1H-pyrazol-4-yl)pyridin-4-yloxy)benzenamine (0.07 g, 0.23 mmol) and triethylamine (0.05 g, 0.5 mmol) in THF (2 mL). The resultant suspension was stirred at RT for 1 h. The solvent was removed in vacuo and the crude residue was purified by silica gel chromatography (MeOH/CH$_2$Cl$_2$) to afford N-(2,5-difluoro-4-(3-(1-methyl-1H-pyrazol-4-yl)pyridin-4-yloxy)phenyl)-4-ethoxy-1-(4-fluorophenyl-2-oxo-1,2-dihydropyridine-3-carboxamide as white solid (76 mg, 58% yield). $^1$H NMR (400 MHz, DMSO-d$_6$): δ 11.23 (s, 1H), 8.85 (s, 1H), 8.40 (dd, J=11.6 Hz, 7.6 Hz, 1H), 8.25 (s, 1H), 8.23 (s, 1H), 8.01 (s, 1H), 7.92 (d, J=7.2 Hz, 1H), 7.48 (m, 2H), 7.36 (m, 2H), 6.75 (d, J=6.4 Hz, 1H), 6.55 (d, J=8.0 Hz, 1H), 5.74 (s 1H), 4.27 (q, J=7.2 Hz, 2H), 3.88 (s, 3H), 1.33 (q, J=7.2 Hz, 3H); MS (ESI) m/z: 562.2 (M+H$^+$).

Example 5

Example B1 (0.052 g, 0.22 mmol), Example A4 (0.07 g, 0.22 mmol), triethylamine (0.06 ml, 0.45 mmol), and TBTU (0.15 g, 0.45 mmol) were combined in DMF (1 mL) and the resultant mixture was stirred at RT for 4 days. The solvent was removed under vacuum and the residue was purified by silica gel chromatography (MeOH/CH$_2$Cl$_2$) to afford N-(4-(2-amino-3-(1-methyl-1H-pyrazol-4-yl)pyridin-4-yloxy)-2,5-difluorophenyl)-1-(4-fluorophenyl)-2-oxo-1,2-dihydropyridine-3-carboxamide as white solid (67 mg, 56.2% yield). 1H NMR (400 MHz, DMSO-d$_6$): δ 12.35 (s, 1H), 8.59 (dd, J=7.2 Hz, 2.0 Hz, 1H), 8.47 (dd, J=12.4 Hz, 7.6 Hz, 1H), 8.14 (dd, J=6.8 Hz, 2.4 Hz, 1H), 7.87 (s, 1H), 7.74 (d, J=5.6 Hz, 1H), 7.58 (m, 3H), 7.41 (m, 3H), 6.72 (t, J=7.2 Hz, 1H), 5.99 (d, = 5.6 Hz, 1H), 5.70 (s, 2H), 3.84 (s, 3H); MS (ESI) ink: 533.2 (M+H$^+$).

Example 6

A solution of Example 132 (0.400 g, 1.443 mmol) in thionyl chloride (2.00 mL) was heated at 60° C. for 1 hour. The solvent was completely removed under vacuum. The residue was co-evaporated from hexane three times to provide 4-ethoxy-1-(4-fluorophenyl)-2-oxo-1,2-dihydropyridine-3-carbonyl chloride (1.529 mmol, 106% yield) as pale pink solid. (0.452 g), suitable for use in the next reaction. MS (ESI) m/z: 292.1 (M+H$^+$).

To a solution of 4-ethoxy-1-(4-fluorophenyl)-2-oxo-1,2-dihydropyridine-3-carbonyl chloride (0.275 g, 0.929 mmol) in CH$_2$Cl$_2$ (2 mL) was added a suspension of 5-chloro-2-fluoro-4-(3-(1-methyl-1H-pyrazol-4-yl)pyridin-4-yloxy) benzenamine (0.148 g, 0.464 mmol) in pyridine (2.00 mL) at 0° C. The resultant mixture was stirred at ambient temp for 30 min. The solvent was completely evaporated and the residue was stirred in water. The precipitate was collected by filtration and was re-crystallized from acetonitrile to provide N-(5-chloro-2-fluoro-4-(3-(1-methyl-1H-pyrazol-4-yl)pyridin-4-yloxy)phenyl)-4-ethoxy-1-(4-fluorophenyl)-2-oxo-1,2-dihydropyridine-3-carboxamide (0.101 g, 37.6% yield) as an off-white solid. The mesylate salt was prepared by treatment with one equivalent of methanesulfonic acid. $^1$H NMR (400 MHz, DMSO-d$_6$) δ 11.40 (s, 1H), 9.20 (s, 1H), 8.62 (d, J=5.5 Hz, 1H), 8.51 (m, 1H), 8.47 (s, 1H), 8.23 (s, 1H), 8.00 (d, J=8.0 Hz, 1H), 7.75 (d, J=11 Hz, 2H), 7.50 (m, 2H), 7.41 (m, 2H), 7.25 (d, J=2.5 Hz, 1H), 6.60 (d, J=5.5 Hz, 1H), 4.30 (q, J=6 Hz, 2H), 3.92 (s, 3H), 2.30 (s, 3H), 1.30 (t, J=6 Hz, 3H); MS (ESI) m/z: 578.2 (M+H$^+$).

Example 7

Example B3 (115 mg, 0.464 mmol), Example A3 (70 mg, 0.232 mmol), TBTU (223 mg, 0.696 mmol) and Et$_3$N (0.194 ml, 1.392 mmol) were combined in DMF (5 mL) and stirred at RT overnight. The completed reaction was diluted with satd. NaHCO$_3$ and extracted with EtOAc (2×). The combined organics were washed with satd. NaHCO$_3$ (1×), brine (1×), and dried (Na$_2$SO$_4$), filtered and evaporated to afford crude product. This was purified by silica gel chromatography (10%-100% EtOAc/hexanes; then 100% THF) to afford N-(2, 5-difluoro-4-(3-(1-methyl-1H-pyrazol-4-yl)pyridin-4-yloxy)phenyl)-5-(4-fluorophenyl)-1-methyl-4-oxo-1,4-dihydropyridine-3-carboxamide (77 mg, 62.5% yield) as a white solid. $^1$H NMR (400 MHz, DMSO-d$_6$): δ 13.47 (s, 1H); 8.81 (s, 1H); 8.67 (d, J=2.3 Hz, 1H); 8.53 (dd, J=12.6, 7.2 Hz, 1H); 8.19-8.23 (m, 2H); 8.12 (d, J=2.3 Hz, 1H); 7.98 (s, 1H); 7.64-7.65 (m, 2H); 7.58 (dd, J=11.0, 7.3 Hz, 1H); 7.23 (t, J=8.9 Hz, 2H); 6.74 (d, J=5.7 Hz, 1H); 3.87 (s, 3H); 3.84 (s, 3H); MS (ESI) m/z: 532.2 (M+H$^+$).

Example 8

Using the method of Example 4, thionyl chloride (5 mL) and Example B2 (0.19 g, 0.7 mmol) were combined to prepare 4-ethoxy-1-(4-fluorophenyl)-2-oxo-1,2-dihydropyridine-3-carbonyl chloride as a solid. This solid was dissolved in THF (3 mL) and added to a solution of Example A6 (0.18 g, 0.35 mmol) and Et$_3$N (0.2 ml, 1.4 mmol) in THF (3 mL). The resultant mixture was stirred at RT for 2 h. The mixture was partitioned between EtOAc (20 mL) and sat aq NaHCO$_3$ (30 mL). The aqueous layer was further extracted with EtOAc (15 ml) and the combined organics were washed with brine, dried (Na$_2$SO$_4$) and concentrated in vacuo. The residue was purified by silica gel chromatography (EtOAc-hexanes) to afford N-(4-(2-[bis[(1,1-dimethylethoxy)carbonyl]amino]-3-(1-methyl-1H-pyrazol-4-yl)pyridin-4-yloxy)-2,5-difluorophenyl)-4-ethoxy-1-(4-fluorophenyl)-2-oxo-1,2-dihydropyridine-3-carboxamide as colorless foam (175 mg, 65% yield). $^1$H NMR (400 MHz, DMSO-d$_6$): δ 11.22 (s, 1H), 8.33 (dd, J=12.7 Hz, 7.2 Hz, 1H), 8.20 (d, J=5.7 Hz, 1H), 7.92 (d, J=7.8 Hz, 1H), 7.87 (s, 1H), 7.48 (m, 4H), 7.36 (t, J=8.8 Hz, 2H), 6.83 (d, J=5.6 Hz, 1H), 6.55 (d, J=7.9 Hz, 1H), 4.28 (q, J=7.0 Hz, 2H), 3.86 (s, 3H), 1.33 (t, J=7.1 Hz, 3H), 1.26 (s, 18H); MS (ESI) m/z: 777.2 (M+H$^+$).

TFA (1 mL) was added to a solution of N-(4-(2-[bis[(1,1-dimethylethoxy)carbonyl]amino]-3-(1-methyl-1H-pyrazol-4-yl)pyridin-4-yloxy)-2,5-difluorophenyl)-4-ethoxy-1-(4-fluorophenyl)-2-oxo-1,2-dihydropyridine-3-carboxamide (0.17 g, 0.22 mmol) in CH$_2$Cl$_2$ (3 mL) and the mixture was stirred at RT for 1 h. The solvent was removed and the residue was partitioned between satd NaHCO$_3$ solution (30 mL) and EtOAc (30 mL). The aqueous layer was extracted with EtOAc (25 mL) and the combined organics were washed with brine, dried (Na$_2$SO$_4$) and concentrated under reduced pressure to afford N-(4-(2-amino-3-(1-methyl-1H-pyrazol-4-yl)pyridin-4-yloxy)-2,5-difluorophenyl)-4-ethoxy-1-(4-fluorophenyl)-2-oxo-1,2-dihydropyridine-3-carboxamide (120 mg, 95% yield) as an off-white solid. $^1$H NMR (400 MHz, DMSO-d$_6$): δ 11.12 (s, 1H), 8.24 (t, J=9.8 Hz, 1H), 7.91 (d, J=7.8 Hz, 1H), 7.87 (s, 1H), 7.74 (d, J=5.8 Hz, 1H), 7.58 (s, 1H), 7.47 (m, 2H), 7.36 (t, J=8.7 Hz, 3H), 6.54 (d, J=7.9 Hz, 1H), 5.98 (d, J=5.8 Hz, 1H), 5.69 (s, 2H), 4.27 (q, J=7.0 Hz, 2H), 3.85 (s, 3H), 1.32 (t, J=7.0 Hz, 3H); MS (ESI) m/z: 577.2 (M+H$^+$).

Example 9

A suspension of 4-ethoxy-1-(4-fluorophenyl)-2-oxo-1,2-dihydropyridine-3-carbonyl chloride (freshly prepared from Example B2 (0.207 g, 0.747 mmol) using the method of Example 4) in THF (5 ml) was added to a 0° C. solution of Example A2 (0.15 g, 0.498 mmol) and N,N-diisopropylethylamine (0.870 ml, 4.98 mmol) in THF (5 ml). The mixture was allowed to warm to room temperature and stir overnight. Additional 4-ethoxy-1-(4-fluorophenyl)-2-oxo-1,2-dihydropyridine-3-carbonyl chloride [freshly prepared from Example B2 (0.207 g, 0.747 mmol)] was added and the mixture was stirred overnight at RT. Additional 4-ethoxy-1-(4-fluorophenyl)-2-oxo-1,2-dihydropyridine-3-carbonyl chloride [freshly prepared from Example B2 (414 mg, 0.996 mmol)] was added to the reaction mixture. After stirring for 3 h, the mixture was partitioned between $CH_2Cl_2$ and sat. $Na_2CO_3$ (aq) and extracted with sat. $Na_2CO_3$ (aq) (2×). The organic extract was dried and evaporated. The crude product was purified by silica gel chromatography (hexanes/EtOAc) to yield N-(4-(3-bromopyridin-4-yloxy)-2,5-difluorophenyl)-4-ethoxy-1-(4-fluorophenyl)-2-oxo-1,2-dihydropyridine-3-carboxamide (0.124 g, 44.4% yield). $^1$H NMR (400 MHz, DMSO-$d_6$): δ 11.24 (s, 1H), 8.74 (s, 1H), 8.37 (m, 2H). 7.92 (d, J=7.8 Hz, 1H), 7.59 (dd. J=10.9, 7.4 Hz, 1H), 7.48 (dd, J=8.8, 4.9 Hz, 2H), 7.36 (t, J=8.7 Hz, 2H), 6.88 (d, J=5.6 Hz, 1H); 6.55 (d, J=7.9 Hz, 1H); 4.28 (q, J=7.0 Hz, 2H); 1.33 (t, J=7.0 Hz, 3H); MS (ESI) m/z: 560.1 (M+H$^+$).

In a sealed tube, N-(4-(3-bromopyridin-4-yloxy)-2,5-difluorophenyl)-4-ethoxy-1-(4-fluorophenyl)-2-oxo-1,2-dihydropyridine-3-carboxamide (0.124 g, 0.221 mmol), 4-(4,4,5,5-tetramethyl-1,3,2-dioxaborolan-2-yl)-1H-pyrazole (0.064 g, 0.332 mmol), potassium carbonate (0.092 g, 0.664 mmol), and tetrakistriphenylphosphine palladium (0) (0.026 g, 0.022 mmol) were suspended in dioxane (6 mL) and water (1.5 mL). The mixture was degassed with Ar and heated at 85° C. overnight. Additional 4-(4,4,5,5-tetramethyl-1,3,2-dioxaborolan-2-yl)-1H-pyrazole (100 mg) and tetrakistriphenylphosphine palladium (0) (0.026 g, 0.022 mmol) were added. The reaction mixture was degassed with Ar and heated at 85° C. for 2 days. The mixture was diluted with EtOAc and extracted with sat. $NaHCO_3$ (aq). The organic extract was washed with brine, dried and evaporated. The crude product was purified by silica gel chromatography (25 g) eluting with $CH_2Cl_2$/MeOH to yield N-(4-(3-(1H-pyrazol-4-yl)pyridin-4-yloxy)-2,5-difluorophenyl)-4-ethoxy-1-(4-fluorophenyl)-2-oxo-1,2-dihydropyridine-3-carboxamide (69 mg, 56.9% yield). The hydrochloride salt was formed by suspending N-(4-(3-(1H-pyrazol-4-yl)pyridin-4-yloxy)-2,5-difluorophenyl)-4-ethoxy-1-(4-fluorophenyl)-2-oxo-1,2-dihydropyridine-3-carboxamide (0.069 g, 0.126 mmol) in acetonitrile (2 ml) and adding 0.1N HCl (1.51 mL, 0.151 mmol). The mixture was sonicated for 10 min. The solution was diluted with water (2 mL), frozen and lyophilized. The crude lyophilate was dried at 80° C. for 4 h under vacuum to yield N-(4-(3-(1H-pyrazol-4-yl)pyridin-4-yloxy)-2,5-difluorophenyl)-4-ethoxy-1-(4-fluorophenyl)-2-oxo-1,2-dihydropyridine-3-carboxamide hydrochloride (0.069 g, 87% yield). $^1$H NMR (400 MHz, DMSO-$d_6$): δ 11.32 (s, 1H); 9.15 (s, 1H); 8.49 (d, J=6.5 Hz, 1H); 8.43 (dd, J=12.5, 7.0 Hz, 1H); 8.33 (s, 2H); 7.93 (d, J=7.8 Hz, 1H); 7.69 (dd, J=10.8, 7.3 Hz, 1H); 7.48 (dd, J=8.8, 4.9 Hz, 2H); 7.37 (t, J=8.8 Hz, 2H); 7.25 (d, J=6.5 Hz, 1H); 6.56 (d, J=7.9 Hz, 1H); 4.28 (q, J=7.0 Hz, 2H); 1.34 (t, J=7.0 Hz, 3H); MS (ESI) m/z: 508.2 (M+H$^+$).

Example 10

Example B3 (0.05 g, 0.2 mmol), Example A6 (0.08 g, 0.15 mmol), TBTU (0.15 g, 0.46 mmol), and $Et_3N$ (0.1 g, 0.1 mmol) were combined in DMF (2 mL) and the reaction mixture was stirred at RT for 48 h. The mixture was diluted with aq $NaHCO_3$ solution (30 mL) and was extracted with EtOAc (2×25 mL). The combined organics were washed with water (30 mL) and brine, dried ($Na_2SO_4$) and concentrated in vacuo. The residue was purified by silica gel chromatography (EtOAc-hexanes) to provide N-(4-(2-[bis[(1,1-dimethylethoxy)carbonyl]amino]-3-(1-methyl-1H-pyrazol-4-yl)pyridin-4-yloxy)-2,5-difluorophenyl)-5-(4-fluorophenyl)-1-methyl-4-oxo-1,4-dihydropyridine-3-carboxamide (85 mg, 73.6% yield) as white solid. $^1$H NMR (400 MHz, DMSO-$d_6$): δ 13.51 (s, 1H), 8.71 (d, J=2.4 Hz, 1H), 8.56 (dd, J=12.4 Hz, 7.2 Hz, 1H), 8.21 (d, J=5.7 Hz, 1H), 8.16 (d, J=2.3 Hz, 1H), 7.88 (s, 1H), 7.69 (m, 2H), 7.59 (dd, J=11.0 Hz, 7.3 Hz, 1H), 7.50 (d, J=0.7 Hz, 1H), 7.28 (t, J=8.9 Hz, 2H), 6.84 (m, 1H), 3.92 (s, 3H), 3.86 (s, 3H), 1.26 (s, 18H); MS (ESI) m/z: 747.2 (M+H$^+$).

A solution of N-(4-(2-[bis[(1,1-dimethylethoxy)carbonyl]amino]-3-(1-methyl-1H-pyrazol-4-yl)pyridin-4-yloxy)-2,5-difluorophenyl)-5-(4-fluorophenyl)-1-methyl-4-oxo-1,4-dihydropyridine-3-carboxamide (0.115 g, 0.15 mmol) in $CH_2Cl_2$ (5 mL) was treated with TFA (0.35 mL, 4.62 mmol) and the solution was stirred at RT for 3 h. The solvent was removed in vacuo and the residue was partitioned between satd $NaHCO_3$ solution (30 mL) and EtOAc (30 mL1). The aqueous layer was extracted with EtOAc (25 mL) and the combined organics were washed with brine, dried ($Na_2SO_4$) and concentrated in vacuo to afford N-(4-(2-amino-3-(1-methyl-1H-pyrazol-4-yl)pyridin-4-yloxy)-2,5-difluorophenyl)-5-(4-fluorophenyl)-1-methyl-4-oxo-1,4-dihydropyridine-3-carboxamide as off-white solid (82 mg, 97% yield). $^1$H NMR (400 MHz, DMSO-$d_6$): δ 13.43 (s, 1H), 8.70 (d, J=2.4 Hz, 1H), 8.49 (dd, J=12.6 Hz, 7.3 Hz, 1H), 8.15 (d, J=2.3 Hz, 1H), 7.88 (s, 1H), 7.75 (d, J=5.8 Hz, 1H), 7.69 (m, 2H), 7.59 (d, J=0.8 Hz, 1H), 7.41 (dd, J=11.2 Hz, 7.4 Hz, 1H), 7.27 (t, J=8.9 Hz, 2H), 6.00 (d, J=5.8 Hz, 1H), 5.69 (s, 2H), 3.91 (s, 3H), 3.85 (s, 3H); MS (ESI) m/z: 547.1 (M+H$^+$).

Biological Data
c-MET Kinase Assay

Activity of c-MET kinase (Seq. ID No. 2) was determined by following the production of ADP from the kinase reaction through coupling with the pyruvate kinase/lactate dehydrogenase system (e.g., Schindler et al. *Science* 2000; 289, pp. 1938-1942). In this assay, the oxidation of NADH (thus the decrease at A340 nm) was continuously monitored spectrophotometrically. The reaction mixture (100 μl) contained c-MET (c-MET residues: 956-1390, from Invitrogen, catalogue #PV3143, 6 nM), polyE4Y (1 mg/mL), $MgCl_2$ (10 mM), pyruvate kinase (4 units), lactate dehydrogenase (0.7 units), phosphoenol pyruvate (1 mM), and NADH (0.28 mM) in 90 mM Tris buffer containing 0.25 mM DTT, 0.2% octylglucoside and 1% DMSO, pH 7.5. Test compounds were incubated with c-MET (Seq. ID No. 2) and other reaction reagents at 22° C. for 0.5 h before ATP (100 μM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e., with no test compound). $IC_{50}$ values were calculated from a series of percent inhibition values determined at a range of inhibitor concentrations using software routines as implemented in the GraphPad Prism software package.

```
c-MET Kinase
                                            (Seq ID No. 2)
MSYYHHHHHHDYDIPTTENLYFQGAMLVPRGSPWIPFTMKKRKQIKDLGS

ELVRYDARVHTPHLDRLVSARSVSPTTEMVSNESVDYRATFPEDQFPNSS

QNGSCRQVQYPLTDMSPILTSGDSDISSPLLQNTVHIDLSALNPELVQAV

QHVVIGPSSLIVHFNEVIGRGHFGCVYHGTLLDNDGKKIHCAVKSLNRIT
```

-continued

DIGEVSQFLTEGIIMKDFSHPNVLSLLGICLRSEGSPLVVLPYMKHGDLR

NFIRNETHNPTVKDLIGFGLQVAKGMKYLASKKFVHRDLAARNCMLDEKF

TVKVADFGLARDMYDKEYYSVHNKTGAKLPVKWMALESLQTQKFTTKSDV

WSFGVLLWELMTRGAPPYPDVNTFDITVYLLQGRRLLQPEYCPDPLYEVM

LKCWHPKAEMRPSFSELVSRISAIFSTFIGEHYVHVNATYVNVKCVAPYP

SLLSSEDNADDEVDTRPASFWETS.

c-KIT kinase Assay

Activity of c-KIT kinase (Seq. ID No. 1) was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 μl) contained c-KIT (cKIT residues T544-V976, from ProQinase, 5.4 nM), polyE4Y (1 mg/mL), $MgCl_2$ (10 mM), pyruvate kinase (4 units), lactate dehydrogenase (0.7 units), phosphoenol pyruvate (1 mM), and NADH (0.28 mM) in 90 mM Iris buffer containing 0.2% octyl-glucoside and 1% DMSO, pH 7.5. Test compounds were incubated with c-KIT (Seq. ID No. 1) and other reaction reagents at 22° C. for less than 2 min before ATP (200 μM) was added to start the reaction. The absorption at 340 nm was monitored continuously for 0.5 hours at 30° C., on Polarstar Optima plate reader (BMG). The reaction rate was calculated using the 0 to 0.5 h time frame. Percent inhibition was obtained by comparison of reaction rate with that of a control (i.e., with no test compound). $IC_{50}$ values were calculated from a series of percent inhibition values determined at a range of inhibitor concentrations using software routines as implemented in the GraphPad Prism software package.

c-KIT with N-terminal GST fusion
(Seq ID No. 1)
LGYWKIKGLVQPTRLLLEYLEEKYEEHLYERDEGDKWRNKKFELGLEFPN

LPYYIDGDVKLIQSMAIIRYIADKHNMLGGCPKERAEISMLEGAVDIRYG

VSRIAYSKDFETLKVDFLSKLPEMLKMFEDRLCHKTYLNGDHVTHPDFML

YDALDVVLYMDPMCLDAFPKLVCFKKRIEAIPQIDKYLKSSKYIWPLQGW

QATFGGGDHPPKSDLVPRHNQTSLYKKAGSAAAVLEENLYFQGTYKYLQK

PMYEVQWKVVEEINGNNYVYIDPIQLPYDHKWEFPRNRLSFGKTLGAGAF

GKVVEATAYGLIKSDAAMTVAVKMLKPSAHLTEREALMSELKVLSYLGNH

MNIVNLLGACTIGGPTLVITEYCCYGDLLNFLRRKRDSFICSKQEDHAEA

ALYKNLLHSKESSCSDSTNEYMDMKPGVSYVVPTKADKRRSVRIGSYIER

DVTPAIMEDDELALDLEDLLSFSYQVAKGMAFLASKNCIHRDLAARNILL

THGRITKICDFGLARDIKNDSNYVVKGNARLPVKWMAPESIFNCVYTFES

DVWSYGIFLWELFSLGSSPYPGMPVDSKFYKMIKEGFRMLSPEHAPAEMY

DIMKTCWDADPLKRPTFKQIVQLIEKQISESTNHIYSNLANCSPNRQKPV

VDHSVRINSVGSTASSSQPLLVHDDV.

KDR Kinase Assay
Assay K1

The activity of KDR kinase was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 μl) contained KDR (Seq ID No. 3, 1.5 nM to 7.1 nM, nominal concentration), polyE4Y (1 mg/mL), pyruvate kinase (3.5 units), lactate dehydrogenase (5.5 units), phosphoenolpyruvate (1 mM), and NADH (0.28 mM) in 60 mM Tris buffer containing 0.13% octyl-glucoside, 13 mM $MgCl_2$, 6.8 mM DTT, and 3.5% DMSO at pH 7.5. The reaction was initiated by adding ATP (0.2 mM, final concentration). The absorption at 340 nm was continuously monitored for 311 at 30° C. on a Polarstar Optima plate reader (BMG) or instrument of similar capacity. The reaction rate was calculated using the 1 h to 211 time frame. Percent inhibition was obtained by comparison of reaction rate with that of a control (i.e., with no test compound). $IC_{50}$ values were calculated from a series of percent inhibition values determined at a range of inhibitor concentrations using software routines as implemented in the GraphPad Prism software package.

Assay K2

KDR kinase assay K2 is the same as for assay K1 except that (1) a nominal concentration of 2.1 nM of enzyme was employed (2) the reaction was pre-incubated at 30° C. for 2 h prior to initiation with ATP and (3) 1.0 mM ATP (final concentration) was used to initiate the reaction.

Assay K3

KDR kinase assay K3 is the same as for assay K1 except that (1) a nominal concentration of 1.1 nM of enzyme was employed, (2) the buffer components per 100 μl reaction mixture were as follows: 75 mM Tris buffer containing 0.066% octyl-glucoside, 17 mM $MgCl_2$, and 1% DMSO at pH 7.5, (3) the final concentration of DTT was 0.66 mM, (4) the reaction was pre-incubated at 30° C. for 1 h prior to initiation with ATP, and (5) 1.0 mM ATP (final concentration) was used to initiate the reaction.

KUR protein sequence used for screening
(Seq. ID No. 3)
DPDELPLDEHCERLPYDASKWEFPRDRLKLGKPLGRGAFGQVIEADAFGI

DKTATCRTVAVKMLKEGATHSEHRALMSELKILIHIGHHLNVVNLLGACT

KPGGPLMVIVEFCKFGNLSTYLRSKRNEFVPYKVAPEDLYKDFLTLEHLI

CYSFQVAKGMEFLASRKCIHRDLAARNILLSEKNVVKICDFGLARDIYKD

PDYVRKGDARLPLKWMAPETIFDRVYTIQSDVWSFGVLLWEIFSLGASPY

PGVKIDEEFCRRLKEGTRMRAPDYTTPEMYQTMLDCWHGEPSQRPTFSEL

VEHLGNLLQANAQQD

FMS Kinase Assay

Activity of FMS kinase was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 μl) contained FMS (purchased from Invitrogen or Millipore, 6 nM), polyE4Y (1 mg/mL), $MgCl_2$ (10 mM), pyruvate kinase (4 units), lactate dehydrogenase (0.7 units), phosphoenol pyruvate (1 mM) and NADH (0.28 mM) and ATP (500 μM) in a 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on a Polarstar Optima or Synergy 2 plate reader. The reaction rate was calculated using the 2 to 3 h time frame. Percent inhibition was obtained by comparison of reaction rate with that of a control (i.e., with no test compound). $IC_{50}$ values were calculated from a series of percent inhibition values determined at a range of inhibitor concentrations using software routines as implemented in the GraphPad Prism software package.

EBC-1 Cell Culture

EBC-1 cells (catalog #JCRB0820) were obtained from the Japan Health Science Research Resources Bank, Osaka, Japan. Briefly, cells were grown in DMEM supplemented with 10% characterized fetal bovine serum (Invitrogen, Carlsbad, Calif.) at 37° C., 5% $CO_2$, 95% humidity. Cells were allowed to expand until reaching 70-95% confluency at which point they were subcultured or harvested for assay use.

EBC-1 Cell Proliferation Assay

A serial dilution of test compound was dispensed into a 96-well black clear bottom plate (Corning, Corning, N.Y.). For each cell line, five thousand cells were added per well in 200 μL complete growth medium. Plates were incubated for 67 hours at 37° C., 5% $CO_2$, 95% humidity. At the end of the incubation period 40 μL of a 440 μM solution of resazurin (Sigma, St. Louis, Mo.) in PBS was added to each well and incubated for an additional 5 hours at 37° C., 5% $CO_2$, 95% humidity. Plates were read on a Synergy2 reader (Biotek, Winooski, Vt.) using an excitation of 540 nM and an emission of 600 nM. Data was analyzed using Prism software (GraphPad, San Diego, Calif.) to calculate $IC_{50}$ values.

MKN-45 Cell Culture

MKN-45 cells (catalog #JCRB0254) were obtained from the Japan Health Science Research Resources Bank, Osaka, Japan. Briefly, cells were grown in RPMI 1640 media supplemented with 10% characterized fetal bovine serum (Invitrogen, Carlsbad, Calif.) at 37° C., 5% CO2, 95% humidity. Cells were allowed to expand until reaching 70-95% confluency at which point they were subcultured or harvested for assay use.

MKN-45 Cell Proliferation Assay

A serial dilution of test compound was dispensed into a 96-well black clear bottom plate (Corning, Corning, N.Y.). Five thousand cells were added per well in 200 μL complete growth medium. Plates were incubated for 67 hours at 37° C., 5% $CO_2$, 95% humidity. At the end of the incubation period 40 μL, of a 440 μM solution of resazurin (Sigma, St. Louis, Mo.) in PBS was added to each well and plates were incubated for an additional 5 h at 37° C., 5% $CO_2$, 95% humidity. Plates were read on a Synergy2 reader (Biotek, Winooski, Vt.) using an excitation of 540 nM and an emission of 600 nM. Data was analyzed using Prism software (GraphPad, San Diego, Calif.) to calculate $IC_{50}$ values.

Compounds of Formula I were found to exhibit inhibitory activity in one or more of the aforementioned assays when evaluated at concentrations ≤10 μM. In some embodiments, compounds of Formula I exhibit greater inhibitory activity against cMET than inhibition of cKIT, KDR, FMS

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A compound of Formula I,

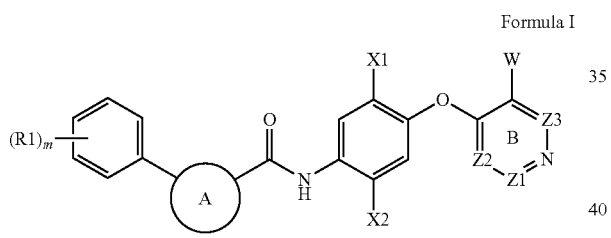

Formula I or a pharmaceutically acceptable salt, enantiomer, stereoisomer or tautomer thereof, wherein:

A is

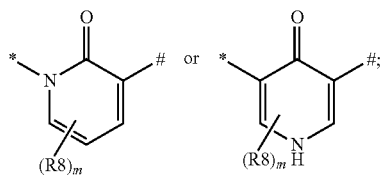

wherein the "*" is connected to the R1-substituted phenyl ring and the "#" is connected to the amide carbonyl;

W is —$(CH_2)_m$-pyrazole optionally substituted with —$(R25)_m$;

X1 is halogen or C1-C6 alkyl;

X2 is halogen or C1-C6 alkyl;

each R1 is individually and independently halogen, H, C1-C6 alkyl, C3-C8 branched alkyl, C3-C8 cycloalkyl, C1-C6 alkoxy, branched C3-C6 alkoxy, or cyano;

Z1 and Z2 are independently and individually CR2 or N;

Z3 is CR3 or N;

with the proviso that ring B is a monocyclic ring which is not a tetrazine;

each R2 is individually and independently H, halogen, C1-C6 alkyl, C3-C8 branched alkyl, C3-C8 cycloalkyl, C1-C6 alkoxy, branched C3-C6 alkoxy, or cyano;

R3 is —NHR4, H, —NR6(R7), C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-$SO_2$—C1-C6-alkyl-, (R7)R6N—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, wherein aryl is phenyl, naphthyl, tetrahydronaphthyl, indenyl or indanyl; and each alkyl or alkylene is optionally substituted with one or two C1-C6 alkyl;

R4 is H, C1-C8 alkyl, C3-C8 cycloalkyl, —$(CH_2)_m$—C(O)R5, —$(CH_2)_p$—OR6, —$(CH_2)_p$—NR6(R7), —$(CH_2)_p$—CN, —$(CH_2)_p$—$SO_2$—C1-C6-alkyl, C6-C10 aryl, —$(CH_2)_m$—C5-C6-heteroaryl, —$(CH_2)_m$—C4-C6-heterocyclyl, —$(CH_2)_m$—C(O)N(R6)-C4-C6-heterocyclyl, or —$(CH_2)_m$—C(O)N(R6)-C5-C6-heteroaryl, wherein each alkyl or alkylene is optionally substituted with one or two C1-C6 alkyl;

R5 is C1-C7 alkyl, branched C3-C8 alkyl, C3-C8 cycloalkyl, —$(CH_2)_m$—OR6, —$(CH_2)_m$—NR6(R7), C6-C10 aryl, —$(CH_2)_m$—C5-C6-heteroaryl, or —$(CH_2)_m$—C4-C6-heterocyclyl, wherein aryl is phenyl, naphthyl, tetrahydronaphthyl, indenyl or indanyl; and each alkyl or alkylene is optionally substituted with one or two C1-C6 alkyl;

each R6 and R7 is individually and independently H, C1-C6 alkyl, or branched C3-C8 alkyl;

each R8 is individually and independently C1-C6 alkoxy, H, halogen, C1-C6 alkyl, C3-C8 branched alkyl, C3-C8 cycloalkyl, branched C3-C6 alkoxy, or cyano;

each alkynyl, cycloalkyl, aryl, heteroaryl and heterocyclyl is independently and optionally substituted with —$(R25)_m$;

each R25 is individually and independently C1-C6 alkyl, branched C3-C8 alkyl, halogen, —$(CH_2)_m$—CN, —(CH$_2$)$_m$—OR6, —(CH$_2$)$_m$—NR6(R7), —(CH$_2$)$_m$—SO$_2$—C1-C6-alkyl, —(CH$_2$)$_m$—C(O)NR6(R7), —(CH$_2$)$_m$—C(O)—C4-C6-heterocyclyl, or —(CH$_2$)$_m$—C4-C6-heterocyclyl, wherein each alkyl or alkylene is optionally substituted with one or two C1-C6 alkyl;

each m is individually and independently 0, 1, 2, or 3;

n is 0, 1, or 2; and each p is individually and independently 1, 2, or 3.

2. The compound of claim 1, wherein the compound is a compound of Formula Ia,

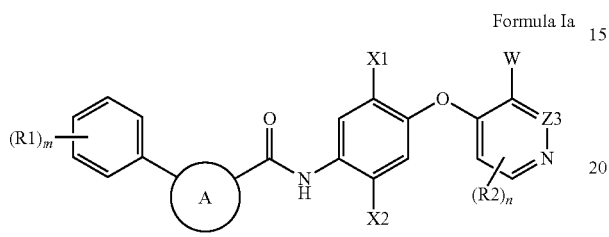

Formula Ia or a pharmaceutically acceptable salt, enantiomer, stereoisomer or tautomer thereof.

3. The compound of claim 2, wherein the compound is a compound of Formula Ib, Formula Ib or a pharmaceutically acceptable salt, enantiomer stereoisomer or tautomer thereof.

4. The compound of claim 3, wherein R3 is —NHR4.

5. The compound of claim 3, wherein R3 is H.

6. The compound of claim 3, wherein R3 is —NR6(R7), (R7)R6N—C1-C6-alkyl, C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, and wherein each alkyl or alkylene is optionally substituted with one or two C1-C6 alkyl.

7. The compound of claim 3, wherein W is

8. The compound of claim 2, wherein Z3 is CR3 and W is

9. The compound of claim 8, wherein the A ring is and wherein R8 is C1-C6 alkoxy.

10. The compound of claim 9, wherein the R8 is ethoxy.

11. The compound of claim 1, wherein Z1 is CR2, Z2 is N, and Z3 is CR3.

12. The compound of claim 11, wherein the compound is a compound of Formula Id, Formula Id or a pharmaceutically acceptable salt, enantiomer, stereoisomer or tautomer thereof.

13. The compound of claim 12, wherein R3 is —NHR4.

14. The compound of claim 12, wherein R3 is H.

15. The compound of claim 12, wherein R3 is —NR6(R7), C1-C8 alkyl, C2-C3 alkynyl, C3-C8 cycloalkyl, C1-C6-alkoxy-C1-C6-alkyl-, hydroxy-C1-C6-alkyl-, cyano, cyano-C1-C6-alkyl-, C1-C6-SO$_2$—C1-C6-alkyl-, (R7)R6N—C1-C6-alkyl-, C4-C6-heterocyclyl, C4-C6-heterocyclyl-C1-C6-alkyl-, C6-C10 aryl, C5-C6-heteroaryl, or C5-C6-heteroaryl-C1-C6-alkyl-, and wherein each alkyl or alkylene is optionally substituted with one or two C1-C6 alkyl.

16. The compound of claim 12, wherein W is

17. The compound of claim 11, wherein W is

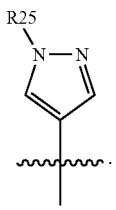

18. The compound of claim 16 or 17, wherein the A ring is

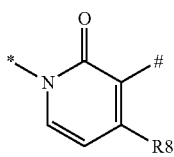

and wherein R8 is C1-C6 alkoxy.

19. The compound of claim 18, wherein the R8 is ethoxy.

20. A compound selected from the group consisting of N-(2,5-difluoro-4-(5-(1-methyl-1H-pyrazol-4-yl)pyrimidin-4-yloxy)phenyl)-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-1-(4-fluorophenyl)-2-oxo-1,2-dihydropyridine-3-carboxamide, N-(4-(3-(1-(cyanomethyl)-1H-pyrazol-4-yl)pyridin-4-yloxy)-2,5-difluorophenyl)-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(4-(2-amino-3-(1-methyl-1H-pyrazol-4-yl)pyridin-4-yloxy)-2,5-difluorophenyl)-1-(4-fluorophenyl)-2-oxo-1,2-dihydropyridine-3-carboxamide, N-(5-chloro-2-fluoro-4-(3-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(2,5-difluoro-4-(3-(1-methyl-1H-pyrazol-4-yl)pyridin-4-yloxy)phenyl)-5-(4-fluorophenyl)-1-methyl-4-oxo-1,4-dihydropyridine-3-carboxamide, N-(4-(2-amino-3-(1-methyl-1H-pyrazol-4-yl)pyridin-4-yloxy)-2,5-difluorophenyl)-4-ethoxy-1-(4-fluorophenyl)-2-oxo-1,2-dihydropyridine-3-carboxamide, N-(4-(3-(1H-pyrazol-4-yl)pyridin-4-yloxy)-2,5-difluorophenyl)-4-ethoxy-1-(4-fluorophenyl)-2-oxo-1,2-dihydropyridine-3-carboxamide, N-(4-(2-amino-3-(1-methyl-1H-pyrazol-4-yl)pyridin-4-yloxy)-2,5-difluorophenyl)-5-(4-fluorophenyl)-1-methyl-4-oxo-1,4-dihydropyridine-3-carboxamide and pharmaceutically acceptable salts, and tautomers thereof.

21. A pharmaceutical composition, comprising a compound of claim 1 and a pharmaceutically acceptable carrier.

22. The composition of claim 21, further comprising an additive selected from adjuvants, excipients, diluents, or stabilizers.

23. A method of treating rheumatoid arthritis, the method comprising administering to a patient in need thereof an effective amount of a compound of claim 1.

* * * * *

SEQUENCE LISTING

```
<160> NUMBER OF SEQ ID NOS: 3

<210> SEQ ID NO 1
<211> LENGTH: 676
<212> TYPE: PRT
<213> ORGANISM: Artificial Sequence
<220> FEATURE:
<223> OTHER INFORMATION: c-KIT with N-terminal GST fusion

<400> SEQUENCE: 1

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
                20                  25                  30

Glu Gly Asp Lys Trp Arg Asn Lys Lys Phe Glu Leu Gly Leu Glu Phe
            35                  40                  45

Pro Asn Leu Pro Tyr Tyr Ile Asp Gly Asp Val Lys Leu Thr Gln Ser
        50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
                85                  90                  95

Ile Arg Tyr Gly Val Ser Arg Ile Ala Tyr Ser Lys Asp Phe Glu Thr
            100                 105                 110

Leu Lys Val Asp Phe Leu Ser Lys Leu Pro Glu Met Leu Lys Met Phe
        115                 120                 125
```

```
Glu Asp Arg Leu Cys His Lys Thr Tyr Leu Asn Gly Asp His Val Thr
    130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
            180                 185                 190

Tyr Ile Trp Pro Leu Gln Gly Trp Gln Ala Thr Phe Gly Gly Gly Asp
        195                 200                 205

His Pro Pro Lys Ser Asp Leu Val Pro Arg His Asn Gln Thr Ser Leu
210                 215                 220

Tyr Lys Lys Ala Gly Ser Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
                260                 265                 270

Pro Thr Gln Leu Pro Tyr Asp His Lys Trp Glu Phe Pro Arg Asn Arg
            275                 280                 285

Leu Ser Phe Gly Lys Thr Leu Gly Ala Gly Ala Phe Gly Lys Val Val
    290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
                325                 330                 335

Leu Met Ser Glu Leu Lys Val Leu Ser Tyr Leu Gly Asn His Met Asn
                340                 345                 350

Ile Val Asn Leu Leu Gly Ala Cys Thr Ile Gly Gly Pro Thr Leu Val
            355                 360                 365

Ile Thr Glu Tyr Cys Cys Tyr Gly Asp Leu Leu Asn Phe Leu Arg Arg
        370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
                405                 410                 415

Ser Thr Asn Glu Tyr Met Asp Met Lys Pro Gly Val Ser Tyr Val Val
                420                 425                 430

Pro Thr Lys Ala Asp Lys Arg Arg Ser Val Arg Ile Gly Ser Tyr Ile
            435                 440                 445

Glu Arg Asp Val Thr Pro Ala Ile Met Glu Asp Glu Leu Ala Leu
450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
                485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Val Lys Gly Asn
        515                 520                 525

Ala Arg Leu Pro Val Lys Trp Met Ala Pro Glu Ser Ile Phe Asn Cys
    530                 535                 540

Val Tyr Thr Phe Glu Ser Asp Val Trp Ser Tyr Gly Ile Phe Leu Trp
545                 550                 555                 560
```

```
Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
        595                 600                 605

Ala Asp Pro Leu Lys Arg Pro Thr Phe Lys Gln Ile Val Gln Leu Ile
    610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
                645                 650                 655

Ile Asn Ser Val Gly Ser Thr Ala Ser Ser Ser Gln Pro Leu Leu Val
                660                 665                 670

His Asp Asp Val
        675

<210> SEQ ID NO 2
<211> LENGTH: 474
<212> TYPE: PRT
<213> ORGANISM: Homo sapiens

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Leu Val Pro Arg Gly Ser
            20                  25                  30

Pro Trp Ile Pro Phe Thr Met Lys Lys Arg Lys Gln Ile Lys Asp Leu
        35                  40                  45

Gly Ser Glu Leu Val Arg Tyr Asp Ala Arg Val His Thr Pro His Leu
    50                  55                  60

Asp Arg Leu Val Ser Ala Arg Ser Val Ser Pro Thr Thr Glu Met Val
65                  70                  75                  80

Ser Asn Glu Ser Val Asp Tyr Arg Ala Thr Phe Pro Glu Asp Gln Phe
                85                  90                  95

Pro Asn Ser Ser Gln Asn Gly Ser Cys Arg Gln Val Gln Tyr Pro Leu
            100                 105                 110

Thr Asp Met Ser Pro Ile Leu Thr Ser Gly Asp Ser Asp Ile Ser Ser
        115                 120                 125

Pro Leu Leu Gln Asn Thr Val His Ile Asp Leu Ser Ala Leu Asn Pro
    130                 135                 140

Glu Leu Val Gln Ala Val Gln His Val Val Ile Gly Pro Ser Ser Leu
145                 150                 155                 160

Ile Val His Phe Asn Glu Val Ile Gly Arg Gly His Phe Gly Cys Val
                165                 170                 175

Tyr His Gly Thr Leu Leu Asp Asn Asp Gly Lys Lys Ile His Cys Ala
            180                 185                 190

Val Lys Ser Leu Asn Arg Ile Thr Asp Ile Gly Glu Val Ser Gln Phe
        195                 200                 205

Leu Thr Glu Gly Ile Ile Met Lys Asp Phe Ser His Pro Asn Val Leu
    210                 215                 220

Ser Leu Leu Gly Ile Cys Leu Arg Ser Glu Gly Ser Pro Leu Val Val
225                 230                 235                 240

Leu Pro Tyr Met Lys His Gly Asp Leu Arg Asn Phe Ile Arg Asn Glu
                245                 250                 255
```

```
Thr His Asn Pro Thr Val Lys Asp Leu Ile Gly Phe Gly Leu Gln Val
            260                 265                 270

Ala Lys Gly Met Lys Tyr Leu Ala Ser Lys Lys Phe Val His Arg Asp
        275                 280                 285

Leu Ala Ala Arg Asn Cys Met Leu Asp Glu Lys Phe Thr Val Lys Val
    290                 295                 300

Ala Asp Phe Gly Leu Ala Arg Asp Met Tyr Asp Lys Glu Tyr Tyr Ser
305                 310                 315                 320

Val His Asn Lys Thr Gly Ala Lys Leu Pro Val Lys Trp Met Ala Leu
                325                 330                 335

Glu Ser Leu Gln Thr Gln Lys Phe Thr Thr Lys Ser Asp Val Trp Ser
            340                 345                 350

Phe Gly Val Leu Leu Trp Glu Leu Met Thr Arg Gly Ala Pro Pro Tyr
        355                 360                 365

Pro Asp Val Asn Thr Phe Asp Ile Thr Val Tyr Leu Leu Gln Gly Arg
    370                 375                 380

Arg Leu Leu Gln Pro Glu Tyr Cys Pro Asp Pro Leu Tyr Glu Val Met
385                 390                 395                 400

Leu Lys Cys Trp His Pro Lys Ala Glu Met Arg Pro Ser Phe Ser Glu
                405                 410                 415

Leu Val Ser Arg Ile Ser Ala Ile Phe Ser Thr Phe Ile Gly Glu His
            420                 425                 430

Tyr Val His Val Asn Ala Thr Tyr Val Asn Val Lys Cys Val Ala Pro
        435                 440                 445

Tyr Pro Ser Leu Leu Ser Ser Glu Asp Asn Ala Asp Asp Glu Val Asp
    450                 455                 460

Thr Arg Pro Ala Ser Phe Trp Glu Thr Ser
465                 470

<210> SEQ ID NO 3
<211> LENGTH: 315
<212> TYPE: PRT
<213> ORGANISM: Homo sapiens

<400> SEQUENCE: 3

Asp Pro Asp Glu Leu Pro Leu Asp Glu His Cys Glu Arg Leu Pro Tyr
1               5                   10                  15

Asp Ala Ser Lys Trp Glu Phe Pro Arg Asp Arg Leu Lys Leu Gly Lys
            20                  25                  30

Pro Leu Gly Arg Gly Ala Phe Gly Gln Val Ile Glu Ala Asp Ala Phe
        35                  40                  45

Gly Ile Asp Lys Thr Ala Thr Cys Arg Thr Val Ala Val Lys Met Leu
    50                  55                  60

Lys Glu Gly Ala Thr His Ser Glu His Arg Ala Leu Met Ser Glu Leu
65                  70                  75                  80

Lys Ile Leu Ile His Ile Gly His His Leu Asn Val Val Asn Leu Leu
                85                  90                  95

Gly Ala Cys Thr Lys Pro Gly Gly Pro Leu Met Val Ile Val Glu Phe
            100                 105                 110

Cys Lys Phe Gly Asn Leu Ser Thr Tyr Leu Arg Ser Lys Arg Asn Glu
        115                 120                 125

Phe Val Pro Tyr Lys Val Ala Pro Glu Asp Leu Tyr Lys Asp Phe Leu
    130                 135                 140

Thr Leu Glu His Leu Ile Cys Tyr Ser Phe Gln Val Ala Lys Gly Met
145                 150                 155                 160
```

```
Glu Phe Leu Ala Ser Arg Lys Cys Ile His Arg Asp Leu Ala Ala Arg
                165             170             175

Asn Ile Leu Leu Ser Glu Lys Asn Val Val Lys Ile Cys Asp Phe Gly
            180             185             190

Leu Ala Arg Asp Ile Tyr Lys Asp Pro Asp Tyr Val Arg Lys Gly Asp
        195             200             205

Ala Arg Leu Pro Leu Lys Trp Met Ala Pro Glu Thr Ile Phe Asp Arg
    210             215             220

Val Tyr Thr Ile Gln Ser Asp Val Trp Ser Phe Gly Val Leu Leu Trp
225             230             235             240

Glu Ile Phe Ser Leu Gly Ala Ser Pro Tyr Pro Gly Val Lys Ile Asp
                245             250             255

Glu Glu Phe Cys Arg Arg Leu Lys Glu Gly Thr Arg Met Arg Ala Pro
                260             265             270

Asp Tyr Thr Thr Pro Glu Met Tyr Gln Thr Met Leu Asp Cys Trp His
            275             280             285

Gly Glu Pro Ser Gln Arg Pro Thr Phe Ser Glu Leu Val Glu His Leu
    290             295             300

Gly Asn Leu Leu Gln Ala Asn Ala Gln Gln Asp
305             310             315
```